United States Patent
Bell et al.

(10) Patent No.: US 12,234,488 B2
(45) Date of Patent: Feb. 25, 2025

(54) MUTANT REVERSE TRANSCRIPTASE WITH INCREASED THERMAL STABILITY AS WELL AS PRODUCTS, METHODS AND USES INVOLVING THE SAME

(71) Applicant: Roche Diagnostics Operations, Inc., Indianapolis, IN (US)

(72) Inventors: Christian Helmut Bell, Basel (CH); Harald Sobek, Biberach (DE); Heiko Walch, Munich (DE); Kiyoshi Yasukawa, Koyoto (JP); Misato Baba, Hyto (JP)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 150 days.

(21) Appl. No.: 18/068,739

(22) Filed: Dec. 20, 2022

(65) Prior Publication Data

US 2023/0203460 A1 Jun. 29, 2023

Related U.S. Application Data

(60) Division of application No. 16/599,407, filed on Oct. 11, 2019, now Pat. No. 11,618,892, which is a continuation of application No. PCT/EP2018/059170, filed on Apr. 10, 2018.

(30) Foreign Application Priority Data

Apr. 11, 2017 (EP) .................................... 17000621

(51) Int. Cl.
   *C12P 19/34* (2006.01)
   *C12N 9/12* (2006.01)
   *C12Q 1/68* (2018.01)

(52) U.S. Cl.
   CPC ............ *C12N 9/1276* (2013.01); *C12P 19/34* (2013.01); *C12Q 1/68* (2013.01); *C12Y 207/07049* (2013.01)

(58) Field of Classification Search
   USPC ......... 435/6.1, 6.11, 6.12, 91.1, 91.2, 91.51; 436/94, 501
   See application file for complete search history.

(56) References Cited

U.S. PATENT DOCUMENTS

| 8,530,218 B2 | 9/2013 | Ferrari et al. |
| 9,663,770 B2 | 5/2017 | Rogers et al. |
| 10,184,009 B2 | 1/2019 | Ast et al. |

FOREIGN PATENT DOCUMENTS

| CN | 1430670 A | 7/2003 |
| CN | 102414321 A | 4/2012 |
| CN | 106164261 A | 11/2016 |
| WO | WO 01/092500 A1 | 12/2001 |
| WO | 2009125006 A2 | 10/2009 |
| WO | 2015075842 A1 | 5/2015 |

OTHER PUBLICATIONS

Arezi et al., Novel mutations in Moloney Murine Leukemia Virus reverse transcriptase increase thermostability through tighter binding to template-primer; Nucleic Acids Research, 2009, vol. 37, No. 2, pp. 473-481.
Baranauskas et al., Generation and characterization of new highly thermostable and processive M-MuLV reverse transcriptase variants; Protein Engineering, Design & Selection, 2012, vol. 25, No. 10, pp. 657-668.
Bradford Marion M., A Rapid and Sensitive Method for the Quantitation of Microgram Quantities of Protein Utilizing the Principle of Protein-Dye Binding; Analytical Biochemistry, 1976, vol. 72, pp. 248-254.
Gerard et al., The role of template-primer in protection of reverse transcriptase from thermal inactivation; Nucleic Acids Research; 2002, vol. 30, No. 14, pp. 3118-3129.
Kotewicz et al., Cloning and overexpression of Moloney murine leukemia virus reverse transcriptase in *Escherichia coli*; Gene, 1985, vol. 35, pp. 249-258.
Ma et al., Effects of various emulsification methods on the oxidation of methyl linoleate; Bioscience, Biotechnology, and Biochemistry, 2014, vol. 78, No. 1, pp. 147-150.
Mizuno et al., Insight into the Mechanism of th Stabililzation of Moloney Murine Leukaemia Virus Reverse Transcriptase by Eliminating RNase H Activity; Biosci. Biotechmol. Biochem., 2010, vol. 74, No. 2, pp. 440-442.
Shoichet et al., A relationship between protein stability and protein function; Proc. Natl. Acad. Sci., 1995, vol. 92, pp. 452-465.
Yasukawa et al., Increase in thermal stability of Moloney murine leukemia virus reverse transcriptase by site-directred mutagenesis; Journal of Biotechnology, 2010, vol. 150, pp. 299-306.
Baba et al., Further increase in thermostability of Moloney murine leukemia virus reverse transcriptase by mutational combination, Protein Engineering, Design and Selection, 30, 551-557, 2017.
Database Geneseq BCA51017, "MMLV reverse transcriptase mutant protein E286R/E302K/L435R," Jul. 16, 2015.

(Continued)

*Primary Examiner* — Frank W Lu
(74) *Attorney, Agent, or Firm* — Taft Stettinius & Hollister LLP

(57) ABSTRACT

The present invention relates to a mutant reverse transcriptase (RT) with increased thermal stability relative to the wildtype, a nucleic acid encoding the mutant RT, a cell comprising the mutant RT or the nucleic acid, a kit comprising the mutant RT, the use of the mutant RT for cDNA synthesis, method for reverse transcription of RNA comprising synthesizing cDNA with the use of the mutant RT and a method for detecting an RNA marker in a sample with the use of the mutant RT.

4 Claims, 11 Drawing Sheets

Figure 2:
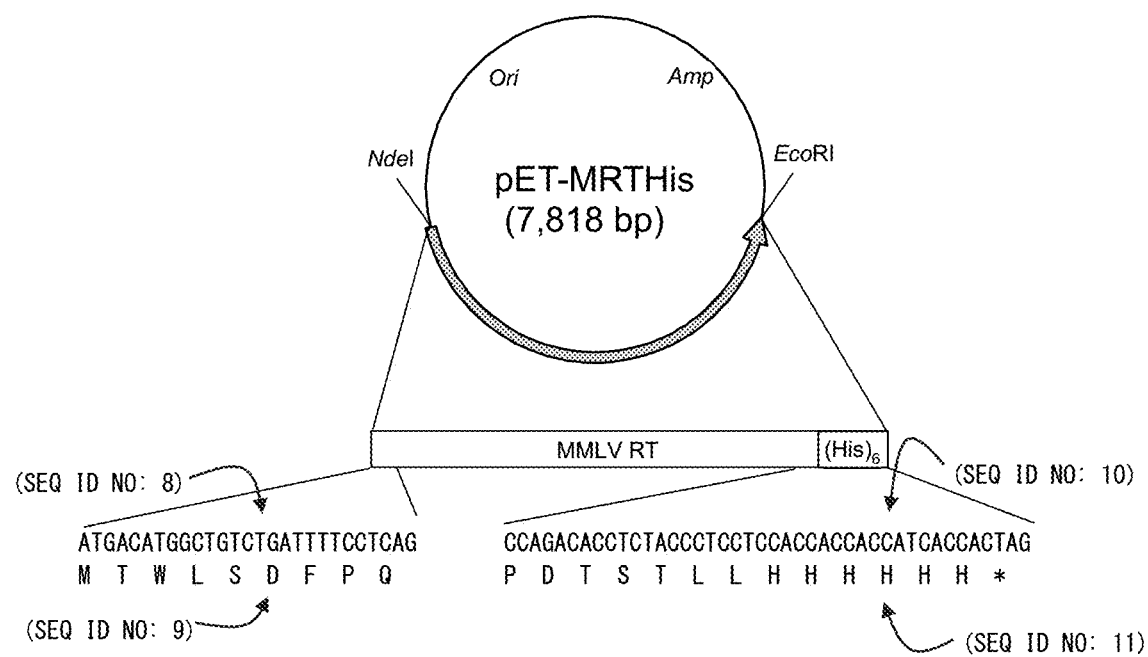

Specification includes a Sequence Listing.

(56) References Cited

OTHER PUBLICATIONS

Cao et al., 2015, Progress in Mucopolysaccharidoses Research, Journal of Qiqihar University of Medicine, 25: 16-23.
Zhu et al., 2015, Analysis of MLC1 gene mutation in a Chinese family with megalen-cephalic eukoencephalopathy with subcortical cysts Chinese Journal of Contemporary Pediatrics, 04: 78-84.

```
1     accctaaatatagaagatgagcatcggctacatgagacctcaaaagagccagatgtttct    60
1      T  L  N  I  E  D  E  H  R  L  H  E  T  S  K  E  P  D  V  S 61    ctagggtccacatggctgtctgattttcctcaggtctggcggaaaccggggcatggga     120
21     L  G  S  T  W  L  S  D  F  P  Q  V  W  A  E  T  G  G  M  G 121   ctggcagttcgccaagctcctctgatcataccrctgaaagcaacctctaccccgtgtcc    180
41     L  A  V  R  Q  A  P  L  I  I  P  L  K  A  T  S  P  V  S 181   ataaaacaataccccatgtcacaagaagccagacggggatcaagccccacatacagaga   240
61     I  K  Q  Y  P  M  S  Q  E  A  R  R  G  I  K  P  H  I  Q  R 241   ctgttggaccagggaatactggtaccctgccagtcccctggaacacgcccctgctaccc   300
81     L  L  D  Q  G  I  L  V  P  C  Q  S  P  W  N  T  P  L  L  P 301   gttaagaaaccagggactaatgattataggcctgtccaggatctgagagaagtcaacaag  360
101    V  K  P  G  T  N  D  Y  R  P  V  Q  D  L  R  E  V  N  K 361   cgggtggaagacatccaccccaccgtgcccaacccttacaacctcttgagcgggctccca  420
121    R  V  E  D  I  H  P  T  V  P  N  P  Y  N  L  L  S  G  L  P 421   ccgtcccaccagtggtacactgtgcttgatttaaaggatgccttttttctgcctgagactc  480
141    P  S  H  Q  W  Y  T  V  L  D  L  K  D  A  F  F  C  L  R  L 481   caccccaccagtcagcctctcttcgcctttgagtggagagatccagagatgggaatctca  540
161    H  P  T  S  Q  P  L  F  A  F  E  W  R  D  P  E  M  G  I  S 541   ggacaattgacctggaccagactcccacagggtttcaaaaacagtccaccctgtttgat   600
181    G  Q  L  T  W  T  R  L  P  Q  G  F  K  N  S  P  T  L  F  D 601   gaggcactgcacagagacctagcagacttccggatccagcacccagacttgatcctgcta  660
201    E  A  L  H  R  D  L  A  D  F  R  I  Q  H  P  D  L  I  L  L 661   cagtacgtggatgacttactgctggccgccacttctgagctagactgccaacaaggtact  720
221    Q  Y  V  D  D  L  L  A  A  T  S  E  L  D  C  Q  Q  G  T 721   cgggccctgttacaaaccctagggaacctcgggtatcgggcctcggccaagaaagcccaa  780
241    R  A  L  L  Q  T  L  G  N  L  G  Y  R  A  S  A  K  K  A  Q 781   atttgccagaaacaggtcaagtatctgggtatcttctaaaagagggtcagagatggctg   840
261    I  C  Q  K  Q  V  K  Y  L  G  Y  L  L  K  E  G  Q  R  W  L 841   actgaggccagaaaacgtactgtgatgggcagcctactccgaagacccctcgacaacta   900
281    T  E  A  R  K  R  T  V  M  G  Q  P  T  P  K  T  P  R  Q  L 901   aggaagttcctagggacggcaggcttctgtcgcctctggatccctgggtttgcagaaatg   960
301    R  K  F  L  G  T  A  G  F  C  R  L  W  I  P  G  F  A  E  M 961   gcagccccttgtaccctctcaccaaaacggggactctgtttaattggggcccagaccaa   1020
321    A  A  P  L  Y  P  L  T  K  T  G  T  L  F  N  W  G  P  D  Q 1021  caaaaggcctatcaagaaatcaagcaagctcttctaactgccccagccctggggttgcca  1080
341    Q  K  A  Y  Q  E  I  K  Q  A  L  L  T  A  P  A  L  G  L  P 1081  gatttgactaagcccttgaactctttgtcgacgagaagcagggctacgccaaaggtgtc  1140
361    D  L  T  K  P  F  E  L  F  V  D  E  K  Q  G  Y  A  K  G  V 1141  ctaacgcaaaaactgggacctcggcgtcggccggtggcctacctgtccaaaaagctagac  1200
381    L  T  Q  K  L  G  P  R  R  R  P  V  A  Y  L  S  K  K  L  D 1201  ccagtagcagctgggtggcccccttgcctacggatggtagcagccattgccgtactgaca  1260
401    P  V  A  A  G  W  P  P  C  L  R  M  V  A  A  I  A  V  L  T
```

*Figure 1*

```
1261  aaggatgcaggcaagctaaccatggacagccactagtcattcgggcccccatgcagta  1320
 421   K  D  A  G  K  L  T  M  G  Q  P  L  V  I  R  A  P  H  A  V 1321  gaggcactagtcaaacaacccccgaccgctggctttccaacgcccggatgactcactat  1380
 441   E  A  L  V  K  Q  P  P  D  R  W  L  S  N  A  R  M  T  H  Y 1381  caggccttgcttttggacacggaccgggtccagttcggaccggtggtagccctgaacccg  1440
 461   Q  A  L  L  L  D  T  D  R  V  Q  F  G  P  V  V  A  L  N  P 1441  gctacgctgctcccactgcctgaggaagggctgcaacacaactgccttgatatcctggcc  1500
 481   A  T  L  L  P  L  P  E  E  G  L  Q  H  N  C  L  D  I  L  A 1501  gaagcccacggaacccgacccgacctaacggaccagccgctcccagacgccgaccacacc  1560
 501   E  A  H  G  T  R  P  D  L  T  D  Q  P  L  P  D  A  D  H  T 1561  tggtacacggatggaagcagtctcttacaagagggacagcgtaaggcgggagctgcggtg  1620
 521   W  Y  T  D  G  S  S  L  L  Q  E  G  Q  R  K  A  G  A  A  V 1621  accacgagaccgaggtaatctgggctaaagccctgccagccgggacatccgctcagcgg  1680
 541   T  T  E  T  E  V  I  W  A  K  A  L  P  A  G  T  S  A  Q  R 1681  gctgaactgatagcactcacccaggccctaaagatggcagaaggtaagaagctaaatgtt  1740
 561   A  E  L  I  A  L  T  Q  A  L  K  M  A  E  G  K  K  L  N  V 1741  tatactgatagccgttatgcttttgctactgcccatatccatggagaaatatacagaagg  1800
 581   Y  T  D  S  R  Y  A  F  A  T  A  H  I  H  G  E  I  Y  R  R 1801  cgtgggttgctcacatcagaaggcaaagagatcaaaaataaagacgagatcttggcccta  1860
 601   R  G  L  L  T  S  E  G  K  E  I  K  N  K  D  E  I  L  A  L 1861  ctaaaagccctctttctgcccaaaagacttagcataatccattgtccaggacatcaaaag  1920
 621   L  K  A  L  F  L  P  K  R  L  S  I  I  H  C  P  G  H  Q  K 1921  ggacacagcgccgaggctagaggcaaccggatggctgaccaagcggcccgaaaggcagcc  1980
 641   G  H  S  A  E  A  R  G  N  R  M  A  D  Q  A  A  R  K  A  A 1981  atcacagagactccagacacctctaccctcctc  2013
 661   I  T  E  T  P  D  T  S  T  L  L
```

**Figure 1 *(continued)***

MUTANT REVERSE TRANSCRIPTASE WITH INCREASED THERMAL STABILITY AS WELL AS PRODUCTS, METHODS AND USES INVOLVING THE SAME

The present invention is a divisional application of U.S. patent application Ser. No. 16/599,407, filed on Oct. 11, 2019, now U.S. Pat. No. 11,618,892 B2, which claims priority to International Patent Application No. PCT/EP2018/059170, filed on Apr. 10, 2018, which claims priority to EP Patent Application No. 17000621.7, filed on Apr. 11, 2017, each of which are hereby incorporated by reference in their entireties.

A computer readable form of the Sequence Listing containing the file named "3003372.0232 Divisional Sequence Listing.xml", which is 16,030 bytes in size (as measured in MICROSOFT WINDOWS® EXPLORER), are provided herein and are herein incorporated by reference. This Sequence Listing consists of SEQ ID NOs:1-11.

The present invention relates to a mutant reverse transcriptase (RT) with increased thermal stability relative to the wildtype, a nucleic acid encoding the mutant RT, a cell comprising the mutant RT or the nucleic acid, a kit comprising the mutant RT, the use of the mutant RT for cDNA synthesis, method for reverse transcription of RNA comprising synthesizing cDNA with the use of the mutant RT and a method for detecting an RNA marker in a sample with the use of the mutant RT.

Reverse transcriptase (RT) [EC 2.7.7.49] is the enzyme responsible for viral genome replication. It possesses RNA- and DNA-dependent DNA polymerase as well as RNase H activities. RTs from Moloney murine leukemia virus (MMLV) and avian myeloblastosis virus (AMV) are widely used in cDNA synthesis because they have high catalytic activity and fidelity. For cDNA synthesis, a higher reaction temperature is desirable because it reduces RNA secondary structures and nonspecific primer binding. Therefore, improving the thermal stability of RT is an important object. The thermal stability of MMLV RT (Kotewicz et al., 1985; Gerard et al., 2002; Mizuno et al., 2010) has been improved by eliminating the RNase H activity. In recent years, the thermal stability of MMLV RT was further improved by introducing positive charges at positions that have been implicated in the interaction with a template-primer (Yasukawa et al., 2010), by random mutagenesis (Arezi and Hogrefe, 2009; Baranauskas et al., 2012) and by changing a surface hydrophobic residue into a hydrophilic one (Konishi et al., 2014). As a result, reaction temperature for cDNA synthesis has increased from 37-45° C. to 50-55° C. However, further stabilization is desired to improve the efficiency of cDNA synthesis.

For various enzymes, site-directed mutagenesis and/or random mutations have been extensively performed, and various mutations which confer the enzymes desirable properties, such as enhanced catalytic activity or thermostability, have been identified. If the effects of these mutations were additive, a variant enzyme with multiple mutations would have more desirable properties. However, it is generally known that there is a compromise between activity and stability in various enzymes: mutations which increase enzyme activity accompany decrease in protein stability, and those which increase protein stability do decrease in enzyme activity (Shoichet et al., 1995). In addition, it is not easy presently to predict the effect of mutational combination on enzyme properties. MM3 (E286R/E302K/L435R) is a thermostable MMLV RT triple variant generated by introducing three mutations aimed to increase positive charges into the wild-type MMLV RT (Yasukawa et al., 2010).

However, it was an object of the present invention to provide further thermostable mutant reverse transcriptases derived from MMLV.

For this, 29 mutations were designed. The corresponding single variants were produced in *Escherichia coli* and characterized for activity and stability, and six mutations (Ala32→Val, Leu41→Asp, Leu72→Arg, Ile212→Arg, Leu272→Glu, and Trp388→Arg) were selected. Fifteen multiple variants were designed by combining one or more of the six mutations with the MM3 mutation. The corresponding multiple variants were produced and characterized. A sextuple variant MM3.14 (A32V/L72R/E286R/E302K/W388R/L435R) exhibited higher thermal stability than the wildtype or mutant MM3 (see Example 2 and FIGS. 4E, 4F, 5 and 6).

Accordingly, in a first aspect the present invention relates to a mutant reverse transcriptase (RT) with increased thermal stability relative to the wildtype RT of SEQ ID NO: 1, the mutant RT comprising i) an amino acid sequence that has six amino acid substitutions relative to wildtype RT of SEQ ID NO: 1, wherein
Ala at position 32 is substituted with Val (A32V);
Leu at position 72 is substituted with Arg (L72R);
Glu at position 286 is substituted with Arg (E286R);
Glu at position 302 is substituted with Lys (E302K);
Trp at position 388 is substituted with Arg (W388R); and
Leu at position 435 is substituted with Arg (L435R), or ii) an amino acid sequence that is at least 95% identical to the amino acid sequence of i) and has the six amino acid substitutions as defined in i), wherein the mutant RT exhibits reverse transcriptase activity.

A reverse transcriptase (RT) is an enzyme used to generate complementary DNA (cDNA) from an RNA template, a process termed reverse transcription. It is mainly associated with retroviruses. However, non-retroviruses also use RT (for example, the hepatitis B virus, a member of the Hepadnaviridae, which are dsDNA-RT viruses, while retroviruses are ssRNA viruses). Retroviral RT has three sequential biochemical activities RNA-dependent DNA polymerase activity, ribonuclease H, and DNA-dependent DNA polymerase activity. These activities are used by the retrovirus to convert single-stranded genomic RNA into double-stranded cDNA which can integrate into the host genome, potentially generating a long-term infection that can be very difficult to eradicate. The same sequence of reactions is widely used in the laboratory to convert RNA to DNA for use in molecular cloning, RNA sequencing, polymerase chain reaction (PCR), or genome analysis. A reverse transcriptase commonly is used in the field is MMLV reverse transcriptase from the Moloney murine leukemia virus.

In accordance with the present invention, the mutant RT exhibits reverse transcriptase activity. This means that the mutant RT is capable of generating a cDNA from an RNA template under suitable conditions. Methods for determining transcriptase activity are described herein and given in the Examples (cf. reverse transcription assay using [$^3$H]-dTTP, reverse transcription assay using fluorescent dye PicoGreen and cDNA synthesis).

Moreover, the mutant reverse transcriptase (RT) has increased thermal stability relative to the wildtype RT of SEQ ID NO: 1. The term "increased thermostability" or "increased thermal stability" relative to the wildtype RT means that the mutant RT is less prone to loss of (enzyme) activity at elevated temperatures (i.e. above room temperature or particularly above 40° C.). Stabilization of enzymes including avoidance of denaturation mechanisms in order to realize their full potential as catalysts is an important goal in biotechnology. Enzyme stabilization has notable importance due to increasing number of enzyme applications. The increase in stability allows for sustained usability (e.g. longer storage, usability for a longer time etc). Moreover, for cDNA synthesis, a higher reaction temperature is desirable because it reduces RNA secondary structures and nonspecific primer binding. Therefore, improving the thermal stability of RT is desirable. Increased stability of the mutant relative to the wildtype can be determined by comparing the remaining activity of both enzymes (wildtype and mutant), e.g. after storage or exposure to a particular condition (e.g. elevated temperature, drying, buffer, or salt) (absolute remaining activity). Alternatively, the stability is improved compared to the wild-type, if the mutant, e.g., has a higher relative remaining activity. Relative remaining activity may be determined by comparing the remaining or residual acidity after incubation at given conditions (e.g. time, temperature) to the initial activity before incubation.

The term enzyme activity and its determination are well-known to the person skilled in the art. Enzyme activity is generally defined as conversion of amount of substrate per time. The SI unit for enzyme activity is katal (1 katal=1 mol s$^{-1}$). A more practical and commonly used value is enzyme unit (U)=1 µmol min$^{-1}$. 1 U corresponds to 16.67 nanokatals and is defined as the amount of the enzyme that catalyzes the conversion of 1 micro mole of substrate per minute. The specific activity of an enzyme is the activity of an enzyme per milligram of total protein (expressed in pmol min$^{-1}$mg$^{-1}$).

The enzyme activity may be determined in an assay measuring either the consumption of substrate or cofactor or the formation of product over time. A large number of different methods of measuring the concentrations of substrates and products exist and many enzymes can be assayed in several different ways as known to the person skilled in the art. In the present invention, the RT in question is, e.g., incubated with an RNA template, primers and a suitable dNTP mixture and the production of cDNA or consumption of dNTP is monitored. Monitoring can, e.g., be done by e.g. measuring UV absorbance at 260 nm, incorporation of labels (e.g. [$^3$H]-dTTP; see Examples), binding of markers to DNA (e.g. PicoGreen®) or PCR (cf. Examples).

In a preferred embodiment of the present invention, increased thermal stability of the mutant RT relative to the respective RT without mutation may be determined and expressed as remaining activity after a stress incubation (e.g. 10 min at e.g. 60° C. or any other condition given in the Examples) in relation to the initial activity before stress incubation (see Examples). For this, the enzymatic reaction may be monitored as detailed above or in the Examples and the change in activity may be calculated. The values obtained for heat-incubated samples may be compared to the respective un-stressed sample (value set to 100% activity) and calculated in percent activity (activity (stressed sample)/activity (unstressed sample)*100). Accordingly, a mutant's value higher than the value obtained with wild-type enzyme represents an improvement in thermal stability. The stability is increased, if [% remaining activity of the mutant]−[% remaining activity of the wild-type]>0. Alternatively, the remaining activity of the mutant may be also expressed as activity in percent and may be calculated as follows: [% remaining activity of the mutant]/[% remaining activity of the wild-type]*100%. The stability of the mutant relative to the wild-type is increased if the resulting value is >100%. Particular suitable tests for determining stability are described in the Examples. The cDNA synthesis test with real-time PCR (see FIG. 5) seems tp provide the most sensitive test.

A suitable method for the determination of increased thermal stability is detailed in the Examples. Exemplary conditions for stress conditions may be preincubation at 48-65° C. (particularly 60° C.) for 10 min and testing afterwards with reverse transcription assay using [$^3$H]-dTTP, reverse transcription assay using fluorescent dye PicoGreen or preferably cDNA synthesis test with real-time PCR.

The RT of the present invention is derived from MMLV RT, which is a 75-kDa monomer. It is comprised of the fingers, palm, thumb, connection, and RNase H domains. The active site of the DNA polymerase reaction resides in the fingers/palm/thumb domain, while that of RNase H reaction lies in the RNase H domain.

The amino acid sequence of the RT referred to as wildtype RT including the numbering of the amino acids is as follows:

```
                                                              (SEQ ID NO: 1)
          TLNIEDEHRL HETSKEPDVS LGSTWLSDFP QAWAETGGMG LAVRQAPLII       60

PLKATSTPVS

IKQYPMSQEA RLGIKPHIQR LLDQGILVPC QSPWNTPLLP VKKPGTNDYR      120

PVQDLREVNK

RVEDIHPTVP NPYNLLSGLP PSHQWYTVLD LKDAFFCLRL HPTSQPLFAF      180

EWRDPEMGIS

GQLTWTRLPQ GFKNSPTLFD EALHRDLADF RIQHPDLILL QYVDDLLLAA      240

TSELDCQQGT

RALLQTLGNL GYRASAKKAQ ICQKQVKYLG YLLKEGQRWL TEARKETVMG      300

QPTPKTPRQL

REFLGTAGFC RLWIPGFAEM AAPLYPLTKT GTLFNWGPDQ QKAYQEIKQA      360

LLTAPALGLP
```

-continued

```
DLTKPFELFV DEKQGYAKGV LTQKLGPWRR PVAYLSKKLD PVAAGWPPCL      420
RMVAAIAVLT
KDAGKLTMGQ PLVILAPHAV EALVKQPPDR WLSNARMTHY QALLLDTDRV      480
QFGPVVALNP
ATLLPLPEEG LQHNCLDILA EAHGTRPDLT DQPLPDADHT WYTDGSSLLQ      540
EGQRKAGAAV
TTETEVIWAK ALPAGTSAQR AELIALTQAL KMAEGKKLNV YTDSRYAFAT      600
AHIHGEIYRR
RGLLTSEGKE IKNKDEILAL LKALFLPKRL SIIHCPGHQK GHSAEARGNR      660
MADQAARKAA
ITETPDTSTL L                                                671
```

The corresponding nucleic acid sequence is as follows:

```
                                                  (SEQ ID NO: 7)
accctaaata tagaagatga gcatcggcta catgagacct caaaagagcc agatgtttct    60
ctagggtcca catggctgtc tgattttcct caggcctggg cggaaaccgg gggcatggga   120
ctggcagttc gccaagctcc tctgatcata cctctgaaag caacctctac ccccgtgtcc   180
ataaaacaat accccatgtc acaagaagcc agactgggga tcaagcccca catacagaga   240
ctgttggacc agggaatact ggtaccctgc cagtccccct ggaacacgcc cctgctaccc   300
gttaagaaac cagggactaa tgattatagg cctgtccagg atctgagaga agtcaacaag   360
cgggtggaag acatccaccc caccgtgccc aacccttaca acctcttgag cgggctccca   420
ccgtcccacc agtggtacac tgtgcttgat ttaaaggatg ccttttttctg cctgagactc   480
caccccacca gtcagcctct cttcgccttt gagtggagag atccagagat gggaatctca   540
ggacaattga cctggaccag actcccacag ggtttcaaaa acagtccac cctgtttgat   600
gaggcactgc acagagacct agcagacttc cggatccagc acccagactt gatcctgcta   660
cagtacgtgg atgacttact gctggccgcc acttctgagc tagactgcca acaaggtact   720
cgggccctgt tacaaaccct agggaacctc gggtatcggg cctcggccaa gaaagcccaa   780
atttgccaga aacaggtcaa gtatctgggg tatcttctaa aagagggtca gagatggctg   840
actgaggcca gaaagagac tgtgatgggg cagcctactc cgaagacccc tcgacaacta   900
agggagttcc tagggacggc aggcttctgt cgcctctgga tccctgggtt tgcagaaatg   960
gcagccccct tgtaccctct caccaaaacg gggactctgt ttaattgggg cccagaccaa  1020
caaaaggcct atcaagaaat caagcaagct cttctaactg ccccagccct ggggttgcca  1080
gatttgacta agccctttga actctttgtc gacgagaagc agggctacgc caaaggtgtc  1140
ctaacgcaaa aactgggacc ttggcgtcgg ccggtggcct acctgtccaa aaagctagac  1200
ccagtagcag ctgggtggcc cccttgccta aggatggtag cagccattgc cgtactgaca  1260
aaggatgcag gcaagctaac catgggacag ccactagtca ttctggcccc ccatgcagta  1320
gaggcactag tcaaacaacc ccccgaccgc tggctttcca acgcccggat gactcactat  1380
caggccttgc ttttggacac ggaccgggtc cagttcggac cggtggtagc cctgaacccg  1440
gctacgctgc tcccactgcc tgaggaaggg ctgcaacaca actgccttga tatcctggcc  1500
gaagcccacg gaacccgacc cgacctaacg gaccagccgc tcccagacgc cgaccacacc  1560
tggtacacgg atggaagcag tctccttacaa gagggacagc gtaaggcggg agctgcggtg  1620
```

```
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata aagacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctacccctc ctc                                2013
```

The term "mutant reverse transcriptase" (RT) relates to a RT enzyme whose amino acid sequence differs from the amino acid sequence of SEQ ID NO: 1 by at least six mutations. As detailed above, the mutant RT of the present invention has six obligatory amino acid substitutions relative to wildtype RT of SEQ ID NO: 1, wherein Ala at position 32 is substituted with Val (A32V);
Leu at position 72 is substituted with Arg (L72R);
Glu at position 286 is substituted with Arg (E286R);
Glu at position 302 is substituted with Lys (E302K);
Trp at position 388 is substituted with Arg (W388R); and
Leu at position 435 is substituted with Arg (L435R).

The amino acid sequence of the mutant RT differing from wildtype RT of SEQ ID NO: 1 by the above six obligatory mutations only is referred to as the amino acid sequence of SEQ ID NO: 2 and is as follows:

```
                                                          (SEQ ID NO: 2)
                                                                      32
          TLNIEDEHRL HETSKEPDVS LGSTWLSDFP QVWAETGGMG LAVRQAPLII      60
          PLKATSTPVS
                                                                      72
          IKQYPMSQEA RRGIKPHIQR LLDQGILVPC QSPWNTPLLP VKKPGTNDYR      120
          PVQDLREVNK
          RVEDIHPTVP NPYNLLSGLP PSHQWYTVLD LKDAFFCLRL HPTSQPLFAF      180
          EWRDPEMGIS
          GQLTWTRLPQ GFKNSPTLFD EALHRDLADF RIQHPDLILL QYVDDLLLAA      240
          TSELDCQQGT
                                                                     286
          RALLQTLGNL GYRASAKKAQ ICQKQVKYLG YLLKEGQRWL TEARKRTVMG      300
          QPTPKTPRQL
                                                                     302
          RKFLGTAGFC RLWIPGFAEM AAPLYPLTKT GTLFNWGPDQ QKAYQEIKQA      360
          LLTAPALGLP
                                                                     388
          DLTKPFELFV DEKQGYAKGV LTQKLGPRRR PVAYLSKKLD PVAAGWPPCL      420
          RMVAAIAVLT
                                                                     435
          KDAGKLTMGQ PLVIRAPHAV EALVKQPPDR WLSNARMTHY QALLLDTDRV      480
          QFGPVVALNP
          ATLLPLPEEG LQHNCLDILA EAHGTRPDLT DQPLPDADHT WYTDGSSLLQ      540
          EGQRKAGAAV
          TTETEVIWAK ALPAGTSAQR AELIALTQAL KMAEGKKLNV YTDSRYAFAT      600
          AHIHGEIYRR
```

-continued

RGLLTSEGKE IKNKDEILAL LKALFLPKRL SIIHCPGHQK GHSAEARGNR      660

MADQAARKAA

ITETPDTSTL L                                                671

The six obligatory mutations are indicated by bold letters with underline and their positions are specified by the respective amino acid numbers.

The corresponding nucleic acid sequence is as follows:

(SEQ ID NO: 3)
```
accctaaata tagaagatga gcatcggcta catgagacct caaaagagcc agatgtttct   60
ctagggtcca catggctgtc tgattttcct caggtctggg cggaaaccgg gggcatggga  120
ctggcagttc gccaagctcc tctgatcata cctctgaaag caacctctac ccccgtgtcc  180
ataaaacaat accccatgtc acaagaagcc agacggggga tcaagcccca catacagaga  240
ctgttggacc agggaatact ggtaccctgc cagtccccct ggaacacgcc cctgctaccc  300
gttaagaaac cagggactaa tgattatagg cctgtccagg atctgagaga agtcaacaag  360
cgggtggaag acatccaccc caccgtgccc aaccettaca acctcttgag cgggctccca  420
ccgtcccacc agtggtacac tgtgcttgat ttaaaggatg cctttttctg cctgagactc  480
caccccacca gtcagcctct cttcgccttt gagtggagag atccagagat gggaatctca  540
ggacaattga cctggaccag actcccacag ggtttcaaaa acagtcccac cctgtttgat  600
gaggcactgc acagagacct agcagacttc cggatccagc acccagactt gatcctgcta  660
cagtacgtgg atgacttact gctggccgcc acttctgagc tagactgcca acaaggtact  720
cgggccctgt tacaaaccct agggaacctc gggtatcggg cctcggccaa gaaagcccaa  780
atttgccaga aacaggtcaa gtatctgggg tatcttctaa aagagggtca gagatggctg  840
actgaggcca gaaaacgtac tgtgatgggg cagcctactc cgaagacccc tcgacaacta  900
aggaagttcc tagggacggc aggcttctgt cgcctctgga tccctgggtt tgcagaaatg  960
gcagccccct tgtaccctct caccaaaacg gggactctgt ttaattgggg cccagaccaa 1020
caaaaggcct atcaagaaat caagcaagct cttctaactg ccccagccct ggggttgcca 1080
gatttgacta gcccctttga actctttgtc gacgagaagc agggctacgc caaaggtgtc 1140
ctaacgcaaa aactgggacc tcggcgtcgg ccggtggcct acctgtccaa aaagctagac 1200
ccagtagcag ctgggtggcc cccttgccta aggatggtag cagccattgc cgtactgaca 1260
aaggatgcag gcaagctaac catgggacag ccactagtca ttcgcgcccc ccatgcagta 1320
gaggcactag tcaaacaacc ccccgaccgc tggctttcca acgcccggat gactcactat 1380
caggccttgc ttttggacac ggaccgggtc cagttcggac cggtggtagc cctgaacccg 1440
gctacgctgc tcccactgcc tgaggaaggg ctgcaacaca actgccttga tatcctggcc 1500
gaagcccacg gaacccgacc cgacctaacg gaccagccgc tcccagacgc cgaccacacc 1560
tggtacacgg atggaagcag tctcttacaa gagggacagc gtaaggcggg agctgcggtg 1620
accaccgaga ccgaggtaat ctgggctaaa gccctgccag ccgggacatc cgctcagcgg 1680
gctgaactga tagcactcac ccaggcccta aagatgcag aaggtaagaa gctaaatgtt 1740
tatactgata gccgttatgc ttttgctact gcccatatcc atggagaaat atacagaagg 1800
cgtgggttgc tcacatcaga aggcaaagag atcaaaaata aagacgagat cttggcccta 1860
```

```
ctaaaagccc tctttctgcc caaaagactt agcataatcc attgtccagg acatcaaaag 1920
ggacacagcg ccgaggctag aggcaaccgg atggctgacc aagcggcccg aaaggcagcc 1980
atcacagaga ctccagacac ctctaccctc ctc                              2013
```

However, the mutant RT may have one or more further amino acid substitutions, additions, deletions or combinations thereof. In accordance with the present invention, the mutant RT of the present invention may also comprise an amino acid sequence that is at least 95% identical to the amino acid sequence of SEQ ID NO: 2 and has the six obligatory amino acid substitutions as defined above (A32V/L72R/E286R/E302K/W388R/L435R).

In one embodiment of the present invention, the mutant RT according to the present invention may comprise one or more amino acid substitution(s), particularly a limited number of substitutions (e.g. up to 30, 20, or especially 10 amino acid substitutions), particularly conservative substitutions. "Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Examples of conservative amino acid substitutions include those listed below:

| Original Residue | Conservative Substitutions |
| --- | --- |
| Ala, Leu, Val, Ile | Other aliphatic (Ala, Leu, Val, Ile) |
|  | Other non-polar (Ala, Leu, Val, Ile, Gly, Met) |
| Gly, Met | Other non-polar (Ala, Leu, Val, Ile, Gly, Met) |
| Asp, Glu | Other acidic (Asp, Glu) |
| Lys, Arg | Other basic (Lys, Arg) |
| Asn, Gln, Ser, Thr | Other polar (Asn, Gln, Ser, Thr) |
| His, Tyr, Trp, Phe | Other aromatic (His, Tyr, Trp, Phe) |
| Cys, Pro | None |

In one embodiment of the present invention, the mutant RT according to the present invention may comprise one or more amino acid addition(s), particularly small (e.g. up to 30, 20 or especially 10 amino acids) internal or terminal amino acid additions.

In one embodiment of the present invention, the mutant RT according to the present invention may comprise one or more amino acid deletion(s), particularly N- and/or C-terminal deletions. The deletions may be small (e.g. up to 5, 4, 3, 2, especially 1 amino acid(s) at each terminus). In a preferred embodiment the mutant RT differs from amino acid sequence of SEQ ID NO: 1 by the deletion of at most five amino acids at the N-terminus of SEQ ID NO: 1 and/or by the deletion of at most five amino acids at the C-terminus of SEQ ID NO: 1—in addition to the obligatory mutations as defined above.

In another embodiment, the sequence of the mutant RT according to the present invention may comprise in addition to the obligatory mutations (substitutions), a combination of one or more deletion(s), substitution(s) or addition(s) as defined above. However, the mutant RT comprises an amino acid sequence that is at least 95% identical to the amino acid sequence of SEQ ID NO: 2.

The term "at least 95% identical" or "at least 95% sequence identity" as used herein means that the sequence of the mutant RT according to the present invention has an amino acid sequence characterized in that, within a stretch of 100 amino acids, at least 95 amino acids residues are identical to the sequence of the corresponding sequence of SEQ ID NO: 2. Sequence identities of other percentages are defined accordingly.

Sequence identity according to the present invention can, e.g., be determined by methods of sequence alignment in form of sequence comparison. Methods of sequence alignment are well known in the art and include various programs and alignment algorithms. Moreover, the NCBI Basic Local Alignment Search Tool (BLAST) is available from several sources, including the National Center for Biotechnology Information (NCBI, Bethesda, Md.) and on the internet, for use in connection with the sequence analysis programs blastp, blastn, blastx, tblastn and tblastx. Percentage of identity of mutants according to the present invention relative to the amino acid sequence of e.g. SEQ ID NO: 2 is typically characterized using the NCBI Blast blastp with standard settings. Alternatively, sequence identity may be determined using the software GENEious with standard settings. Alignment results can be, e.g., derived from the Software Geneious (version R8), using the global alignment protocol with free end gaps as alignment type, and Blosum62 as a cost matrix.

As detailed above, the mutant RT of the present invention comprises an amino acid sequence that is at least 95% identical to the amino acid sequence of SEQ ID NO: 2. In a preferred embodiment, the mutant RT comprises or consists of an amino acid sequence which is at least 96%, 97%, 98%, or 99%, particularly 100% identical to the amino acid sequence of SEQ ID NO: 2. Sequence identity may be determined as described above.

In still another preferred embodiment the mutant RT has an thermal stability relative to mutant MM3 which is equal or even increased wherein MM3 has an amino acid sequence that differs from the one of SEQ ID NO: 1 only by three amino acid substitutions, wherein Glu at position 286 is substituted with Arg (E286R), Glu at position 302 is substituted with Lys (E302K) and Leu at position 435 is substituted with Arg (L435R). MM3 (E286R/E302K/L435R) is a thermostable MMLV RT triple variant generated by introducing three mutations aimed to increase positive charges into the wild-type MMLV RT (Yasukawa et al., 2010).

Preferably, thermal stability is determined by measuring reverse transcriptase activity of the mutant measured after thermal treatment, particularly after incubation at 60° C. for 10 minutes. Additionally or alternatively, thermal stability is increased by at least at least 10%, 20%, 30% or 40%, preferably at least 50% relative to the wildtype RT or mutant MM3. Details on these embodiments are given above.

Also preferably, the reverse transcriptase activity of the mutant RT (unstressed) is at least 50% of the reverse transcriptase activity of the wildtype, particularly at least 60%, more particularly at least 70%, especially at least 80%. Additionally or alternatively, the reverse transcriptase activity is determined by RT-mediated dTTP incorporation at 37° C. (see Examples). Details on the determination of enzyme activity are given above.

In another embodiment, the mutant RT may be fused to a further protein. Fusion proteins are proteins created by joining of two or more originally separate proteins or peptides. This procedure results in a polypeptide with functional properties derived from each of the original proteins. Accordingly, depending on the intended use of the RT it may be combined with a further peptide or protein into a fusion protein. The proteins may be fused via a linker or spacer, which increases the likelihood that that the proteins fold independently and behave as expected. Especially in the case where the linkers enable protein purification, linkers in protein or peptide fusions are sometimes engineered with cleavage sites for proteases or chemical agents that enable the liberation of the two separate proteins. Di- or multimeric fusion proteins can be manufactured through genetic engineering by fusion to the original proteins of peptide domains that induce artificial protein di- or multimerization (e.g., streptavidin or leucine zippers). Fusion proteins can also be manufactured with toxins or antibodies attached to them. Other fusions include the addition the addition of signal sequences, such a lipidation signal, sequence, a secretion signal sequence, a glycosylation signal sequence, a translocation signal peptide etc.

Preferably, the fusion protein of the present invention comprises a tag. Tags are attached to proteins for various purposes, e.g. in order to ease purification, to assist in the proper folding in proteins, to prevent precipitation of the protein, to alter chromatographic properties, to modify the protein or to mark or label the protein.

Examples of tags include Arg-tag, the His-tag, the Strep-tag, the Flag-tag, the T7-tag, the V5-peptide-tag, the GST-tag and the c-Myc-tag. A preferred tag in the present invention is a His-tag consisting of six histidine residues.

In a further aspect, the present invention relates to a nucleic acid encoding the mutant RT of the present invention.

The term "nucleic acid" as used herein generally relates to any nucleotide molecule which encodes the mutant RT of the invention and which may be of variable length. Examples of a nucleic acid of the invention include, but are not limited to, plasmids, vectors, or any kind of DNA and/or RNA fragment (s) which can be isolated by standard molecular biology procedures, including, e.g. ion-exchange chromatography. A nucleic acid of the invention may be used for transfection or transduction of a particular cell or organism.

Nucleic acid molecule of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia.

Furthermore, the nucleic acid molecule encoding the mutant RT of the invention can be functionally linked, using standard techniques such as standard cloning techniques, to any desired sequence, such as a regulatory sequence, leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The nucleic acid of the invention may be comprised in an expression vector, wherein the nucleic acid is operably linked to a promoter sequence capable of promoting the expression of the nucleic acid in a host cell.

As used herein, the term "expression vector" generally refers to any kind of nucleic acid molecule that can be used to express a protein of interest in a cell (see also above details on the nucleic acids of the present invention). In particular, the expression vector of the invention can be any plasmid or vector known to the person skilled in the art which is suitable for expressing a protein in a particular host cell including, but not limited to, mammalian cells, bacterial cell, and yeast cells. An expression construct of the present invention may also be a nucleic acid which encodes a RT of the invention, and which is used for subsequent cloning into a respective vector to ensure expression. A suitable vector is described in the Examples and illustrated in FIG. 2. Plasmids and vectors for protein expression are well known in the art, and can be commercially purchased from diverse suppliers including, e.g., Promega (Madison, Wis., USA), Qiagen (Hilden, Germany), Invitrogen (Carlsbad, Calif., USA), or MoBiTec (Germany). Methods of protein expression are well known to the person skilled in the art and are, e.g., described in Sambrook et al., 2000 (Molecular Cloning: A laboratory manual, Third Edition).

The vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, supra).

As detailed above, the nucleic acid which encodes a mutant RT of the invention is operably linked to sequence which is suitable for driving the expression of a protein in a host cell, in order to ensure expression of the protein. However, it is encompassed within the present invention that the claimed expression construct may represent an intermediate product, which is subsequently cloned into a suitable expression vector to ensure expression of the protein. The expression vector of the present invention may further comprise all kind of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene may be operably linked to an internal ribosome entry site (IRES), which might be either cell cycle-specific or cell cycle-independent.

The term "operably linked" as used herein generally means that the gene elements are arranged as such that they function in concert for their intended purposes, e.g. in that transcription is initiated by the promoter and proceeds through the DNA sequence encoding the protein of the present invention. That is, RNA polymerase transcribes the sequence encoding the fusion protein into mRNA, which in then spliced and translated into a protein.

The term "promoter sequence" as used in the context of the present invention generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The promoter sequence of the present invention can be any kind of promoter sequence known to the person skilled in the art, including, but not limited to, constitutive promoters, inducible promoters, cell cycle-specific promoters, and cell type-specific promoters.

In still another aspect, the present invention relates to a cell comprising the mutant RT of the invention or the nucleic acid of the invention. The cell is preferably a host cell. A "host cell" of the present invention can be any kind of organism suitable for application in recombinant DNA technology, and includes, but is not limited to, all sorts of bacterial and yeast strain which are suitable for expressing one or more recombinant protein(s). Examples of host cells include, for example, various *Bacillus subtilis* or *E. coli* strains. A variety of *E. coli* bacterial host cells are known to a person skilled in the art and include, but are not limited to, strains such as DH5-alpha, HB101, MV1190, JM109, JM101, or XL-1 blue which can be commercially purchased from diverse suppliers including, e.g., Stratagene (CA, USA), Promega (WI, USA) or Qiagen (Hilden, Germany). A particularly suitable host cell is also described in the Examples, namely *E. coli* BL21(DE3) cells. *Bacillus subtilis* strains which can be used as a host cell are commercially available.

The cultivation of host cells according to the invention is a routine procedure known to the skilled person. That is, a nucleic acid encoding a mutant RT of the invention can be introduced into a suitable host cell(s) to produce the respective protein by recombinant means. These host cells can by any kind of suitable cells, preferably bacterial cells such as *E. coli*, which can be easily cultivated. At a first step, this approach may include the cloning of the respective gene into a suitable plasmid vector. Plasmid vectors are widely used for gene cloning, and can be easily introduced, i.e. transformed, into bacterial cells which have been made competent. After the protein has been expressed in the respective host cell, the cells can be broken by means of either chemical or mechanical cell lysis are well known to the person skilled in the art, and include, but are not limited to, e.g. hypotonic salt treatment, detergent treatment, homogenization, or ultrasonification.

The present invention also provides a kit for performing a reverse transcription, comprising the mutant RT of the present invention. Reverse transcription is the synthesis of DNA from an RNA template, which is usually mediated by a reverse transriptase, and produces complementary DNA (cDNA). Reverse transcriptases use an RNA template and a short primer complementary to the 3' end of the RNA to direct the synthesis of the first strand cDNA, which can be used directly as a template for the Polymerase Chain Reaction (PCR). This combination of reverse transcription and PCR (RT-PCR) allows the detection of low abundance RNAs in a sample, and production of the corresponding cDNA, thereby facilitating the cloning of low copy genes. Alternatively, the first-strand cDNA can be made double-stranded using DNA Polymerase I and DNA Ligase. These reaction products can be used for direct cloning without amplification. In this case, RNase H activity, from either the RT or supplied exogenously, is required. Depending on the intended use, the kit may comprise in addition to the mutant RT of the invention further components such as a buffer, one or more primers and a dNTP Mix. The kit may also comprise agents needed for a further reaction such as agents needed for PCR, synthesis of the second DNA strand or amplification (e.g. primers, probes, polymerase or markers). Additionally, the kit may comprise an instruction manual.

In a further aspect the present invention relates to the use of the mutant RT of the present invention for cDNA synthesis. A common technique used to study e.g. gene expression in living cells is to the produce a DNA copy (cDNA) of the cellular complement of RNA. This technique provides a means to study RNA from living cells which avoids the direct analysis of inherently unstable RNA. After optional mRNA isolation (using e.g. methods such as affinity chromatography utilizing oligo dT) oligonucleotide sequences are typically annealed to the mRNA molecules and enzymes with reverse transcriptase activity can be utilized to produce cDNA copies of the RNA sequence, utilizing the RNA/DNA primer as a template. Thus, reverse transcription of mRNA is a key step in many forms of gene expression analyses. Typically, mRNA is reverse transcribed into cDNA for subsequent analysis by primer extension or polymerase chain reaction. In the use of the present invention RNA is contacted with a mutant RT of the present invention and typically a primer sequence which is annealed to an RNA template in order for DNA synthesis to be initiated from the 3' OH of the primer. Primers may be selected to be complementary to, or substantially complementary to, sequences occurring at the 3' end of each strand of the nucleic acid sequence of interest. In an exemplary embodiment, a reverse transcription reaction is carried out using an annealing temperature in a reverse transcriptase reaction of typically about 42 to 65° C. The reverse transcription reaction preferably is carried out at about 50° C. to 60° C. or 60° C. to 65° C.

The present invention further provides a method for reverse transcription of RNA, the method comprising synthesizing cDNA from the RNA with the use of the mutant RT of the present invention. The method may be carried our as detailed with respect to the use of the mutant RT of the present invention for cDNA synthesis.

Furthermore, the present invention further provides a method for detecting an RNA marker in a sample,
a) contacting the sample with the mutant RT of the present invention under conditions conducive to the activity of the mutant RT;
b) synthesizing cDNA from the RNA marker with the use of the mutant RT of the present invention; and
c) detecting the presence of the cDNA synthesized in step b), thereby detecting the RNA marker in the sample.

RNA may be used as a marker in various applications. The RNA detected may be indicative itself or it may be indicative of the presence of DNA or the expression of a gene of interest, which in turn is indicative of a disease, presence of a pathogen etc. The RNA itself could be indicative of the presence of a viral RNA, particularly a retroviral RNA. Retroviruses cause a variety of diseases such as cancer, AIDS, autoimmunity and diseases of central nervous system, bone and joints, such as myeloid leukemia, erythroid leukemia, lymphoid leukemia, lymphoma, sarcoma, mammary carcinoma, renal carcinoma, aplastic anemia, hemolytic anemia, autoimmune disease, immunodeficiency, osteopetrosis, arthritiy, periphal neuropathy, encephalopathy, neurodegeneration, dementia, pneumonia and adenomatosis. Viruses inducing such diseases include human immunodeficiency virus (HIV), human T-lymphotropic virus (HTLV), Rous sarcoma virus (RSV) and murine mammary tumor virus (MMTV). However, the RNA marker may be indicative of gene expression. Many genes are expressed under certain conditions (including disease conditions) or with particular species, only. Accordingly, the presence of a protein (or the corresponding mRNA) may be indicative of a disease status, cell or pathogen—to mention only some. As an example cancer cells are characterized by particular markers, the nucleic acids of which may be used in the detection and quantification of the same. Examples which may be mentioned are: especially oncogenes and tumor suppressor genes such as p53, genes of the ras family erb-B2, c-myc, mdm2, c-fos, DPC4, FAP, nm23, RET, WT1, and the like, LOHs, for example with regard to p53, DCC, APC, Rb and the like and also BRCA1 and BRCA2 in hereditary tumors, microsatellite instability of MSH2, MLH1, WT1 and the like; also tumorous RNAs such as CEA, cytokeratins, e.g. CK20, BCL-2, MUC1, in particular tumor-specific splice variants hereof, MAGE3, Muc18, tyrosinase, PSA, PSM, BA46, Mage-1 and the like, or else morphogenic RNAs such as maspin, hCG, GIP, motilin, hTG, SCCA-1, AR, ER, PR, various hormones and the like;—furthermore, especially RNAs and proteins which affect the metastasizing profile, i.e. the expression of molecules involved in angiogenesis, motility, adhesion and matrix degradation such as bFGF, bFGF-R, VEGF, VEGF-Rs, such as VEGF-R1 or VEGF-R2, E-cadherin, integrins, selectins, MMPs, TIMPs, SF, SF-R and the like, the cell cycle profile or proliferation profile, such as cyclins (e.g. expression ratio of cyclins D, E and B), Ki67, p120, p21, PCNA and the like, or the apoptosis profile, such as FAS (L+R), TNF (L+R), perforin, granzyme B, BAX, bcl-2, caspase 3 and the like. Alternatively, the RNA may be indicative of the DNA of a pathogen other than a retrovirus.

In a first step of the method, a sample is contacted with the mutant RT of the present invention under conditions conducive to the activity of the mutant RT. Suitable conditions are detailed herein and well-known to the person skilled in the art. The sample contacted may be any sample suspected of containing the RNA in question, including a sample from a subject. A sample is a limited quantity of material which is intended to be identical to and represent a larger amount of that material(s). An act of obtaining a sample can be done by a person or automatically. Samples can be taken or provided for testing, analysis, inspection, investigation, demonstration, or trial use. Sometimes, sampling may be continuously ongoing. The sample may comprise or consist of a solid, a liquid or a gas; it may be material of some intermediate characteristics such as gel or sputum, tissue, organisms, or a combination of these. Preferably, the sample is liquid or a suspension which allows for easy distribution.

Even if a material sample is not countable as individual items, the quantity of the sample may still be describable in terms of its volume, mass, size, or other such dimensions. A solid sample can come in one or a few discrete pieces, or can be fragmented, granular, or powdered.

The sample in the present context is a quantity of material that is suspected of containing one or more nucleic acids that are to be detected or measured and quantified. As used herein, the term includes—without limitation—a specimen (e.g., a biopsy or medical specimen), a culture (e.g., microbiological culture) or an environmental sample such as water or soil. Samples may be from a subject, such as an animal or human, they may be fluid, solid (e.g., stool), a suspension or tissue. The term "sample from a subject" includes all biological fluids, excretions and tissues isolated from any given subject. Preferably, the subject is an animal, more preferably a mammal or still more preferably a human. The sample may be obtained from all of the various families of domestic animals, as well as feral or wild animals, including, but not limited to, such animals as ungulates, bear, fish, rodents, etc.

As detailed above, "sample" means a quantity of material that is suspected of containing a nucleic acid of interest that is to be quantified. As used herein, the term includes a specimen (e.g., a biopsy or medical specimen) or a culture (e.g., microbiological culture). Samples may be from a plant or animal, including human, it may be fluid, solid (e.g., stool) or tissue. Samples may include materials taken from a patient including, but not limited to cultures, blood, saliva, cerebral spinal fluid, pleural fluid, milk, lymph, sputum, semen, needle aspirates, and the like. The sample may be obtained from all of the various families of domestic animals, as well as feral or wild animals, including, but not limited to, such animals as ungulates, bear, fish, rodents, etc. In regard to a human sample or "tissue sample" or "patient sample" or "patient cell or tissue sample" or "specimen," each means a collection of similar cells or biological or biochemical compounds obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like.

Examples of samples include, but are not limited to, cell or tissue cultures, blood, blood serum, blood plasma, needle aspirate, urine, semen, seminal fluid, seminal plasma, prostatic fluid, excreta, tears, saliva, sweat, biopsy, ascites, cerebrospinal fluid, pleural fluid, amniotic fluid, peritoneal fluid, interstitial fluid, sputum, milk, lymph, bronchial and other lavage samples, or tissue extract samples. The source of the sample may be solid tissue as from a fresh, frozen and/or preserved organ or tissue sample or biopsy or aspirate; or cells from any time in gestation or development of the subject. In a preferred embodiment of the method, the sample is selected from the group consisting of a body fluid, blood, blood plasma, blood serum, urine, bile, cerebrospinal fluid, a swab, a clinical specimen, an organ sample and a tissue sample, particularly a human, an animal or a plant, especially a human. Alternatively, or additionally, the sample has been obtained from a cell culture, a source suspected of being contaminated or a subject, particularly wherein the subject is selected from the group consisting of a human, an animal and a plant, especially a human.

After step a), cDNA is synthesized from the RNA marker with the use of the mutant RT of the present invention. Details on this step are given above. Thereafter, the presence of the cDNA synthesized is detected, thereby detecting the RNA marker in the sample. Methods for detecting DNA are well-known in the art and include PCR methods, use of specific probes with labels (e.g. radioactive or fluorescent) or intercalating agents. In a preferred embodiment reverse transcriptase in combination with real-time PCR is used for the detection of the RNA marker.

The methods and uses of the invention are of particular interest in the medical field such as in diagnosis or in therapeutic monitoring and may be used in order to detect and/or quantify a nucleic acid of interest indicative of a specific microorganism, cell, virus, bacterium, fungus, mammal species, genetic status or a disease. In accordance with this, the methods may be used in the detection of a pathogen. A pathogen has the potential to cause a disease. Typically pathogen is used to describe an infectious agent such as a virus, bacterium, prion, a fungus, or even another microorganism. Of cause, the methods of the invention may also be used to detect non-pathogenic microorganisms. Accordingly, in another preferred embodiment of the method, the RNA marker is indicative of a microorganism, a cell, a virus, a bacterium, a fungus, a mammal species, a genetic status or a disease.

Exemplary pathogens include without limitation:
Bacterial: *Streptococcus, Staphylococcus, Pseudomonas, Burkholderia, Mycobacterium, Chlamydophila, Ehrlichia, Rickettsia, Salmonella, Neisseria, Brucella, Mycobacterium, Nocardia, Listeria, Francisella, Legionella,* and *Yersinia*
Viral: Adenovirus, *Herpes* simplex, *Varicella-zoster* virus, Cytomegalovirus Papillomavirus, *Hepatitis* B virus *Hepatitis* C virus, *Hepatitis* E virus, Poliovirus, Yellow fever virus, Dengue virus, West Nile virus, TBE virus, HIV, *Influenza* virus, Lassa virus, Rotavirus and Ebola virus Fungal: *Candida, Aspergillus, Cryptococcus, Histoplasma, Pneumocystis* and Stachybotrys
Parasites: protozoan parasites, helminth parasites and arthropod parasites It is evident that the reliable detection and optionally quantification of a pathogen may be of high relevance in the diagnosis of the presence and severity of a disease.

Unless defined otherwise, all technical and scientific terms and any acronyms used herein have the same meanings as commonly understood by one of ordinary skill in the art in the field of the invention. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The invention is not limited to the particular methodology, protocols, and reagents described herein because they may vary. Although any methods and materials similar or equivalent to those described herein can be used in the practice of the present invention, the preferred methods, and materials are described herein. Further, the terminology used herein is for the purpose of describing particular embodiments only and is not intended to limit the scope of the present invention.

As used herein and in the appended claims, the singular forms "a", "an", and "the" include plural reference unless the context clearly dictates otherwise. Similarly, the words "comprise", "contain" and "encompass" are to be interpreted inclusively rather than exclusively. Similarly, the word "or" is intended to include "and" unless the context clearly indicates otherwise. The term "plurality" refers to two or more.

The following Figures and Examples are intended to illustrate various embodiments of the invention. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

FIGURES

FIG. 1: Nucleotide sequence (SEQ ID NO: 3) and amino acid sequence (SEQ ID NO: 2) of mutant RT MM3.14. The six obligatory mutations (substitutions A32V, L72R, E286R, E302K, W388R and L435R) with respect to the wildtype are indicated.

FIG. 2: Expression plasmids for MMLV-RT. The asterisk indicates the termination codon.

Figure 3A:
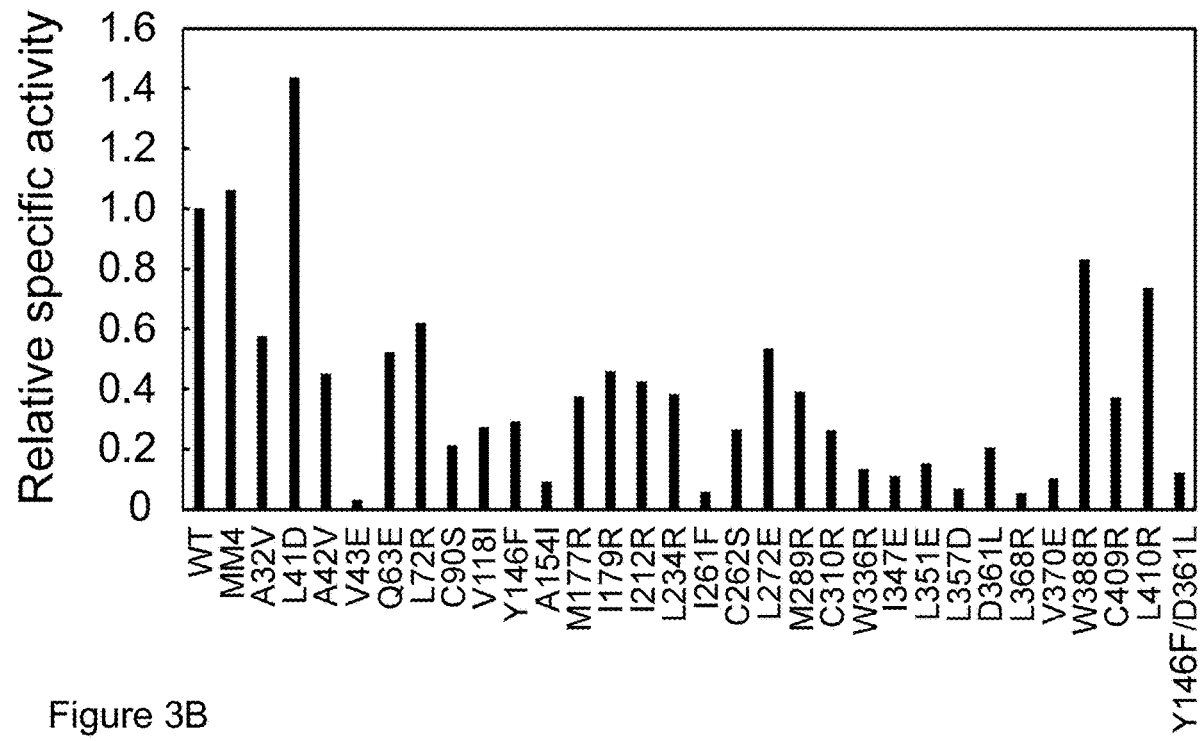
Figure 3B:
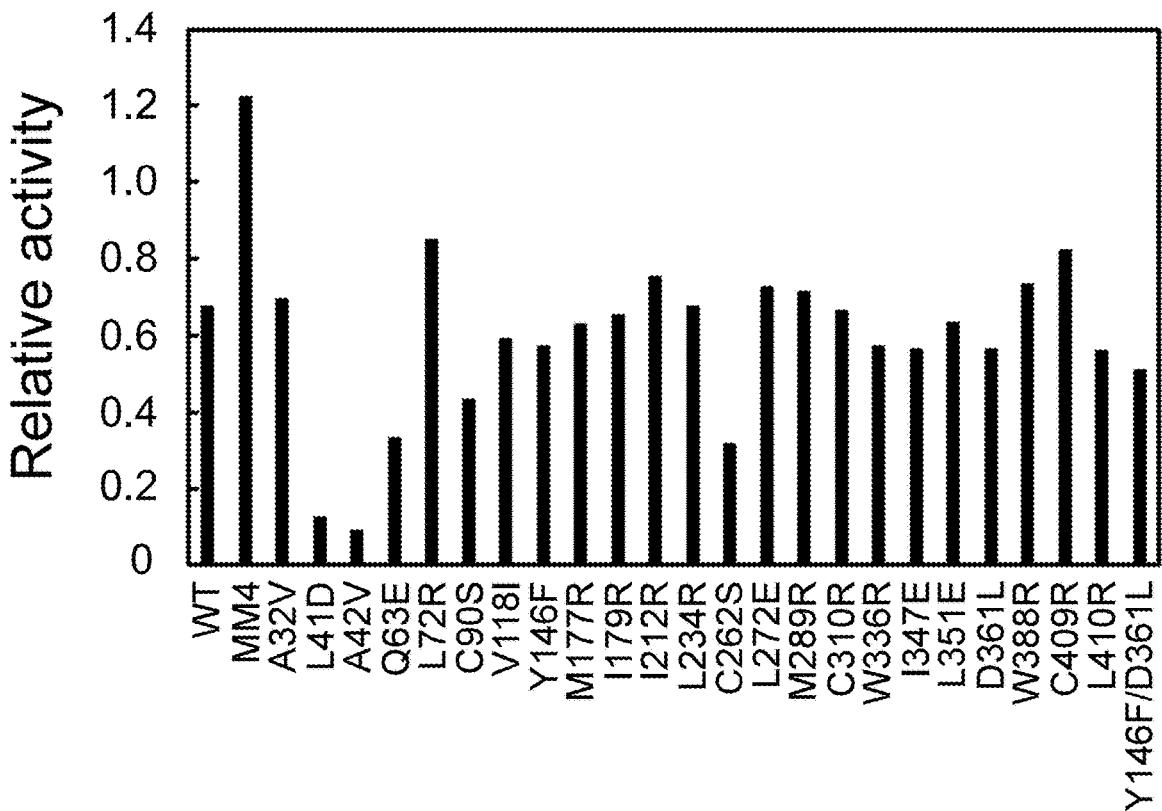
Figure 3C:
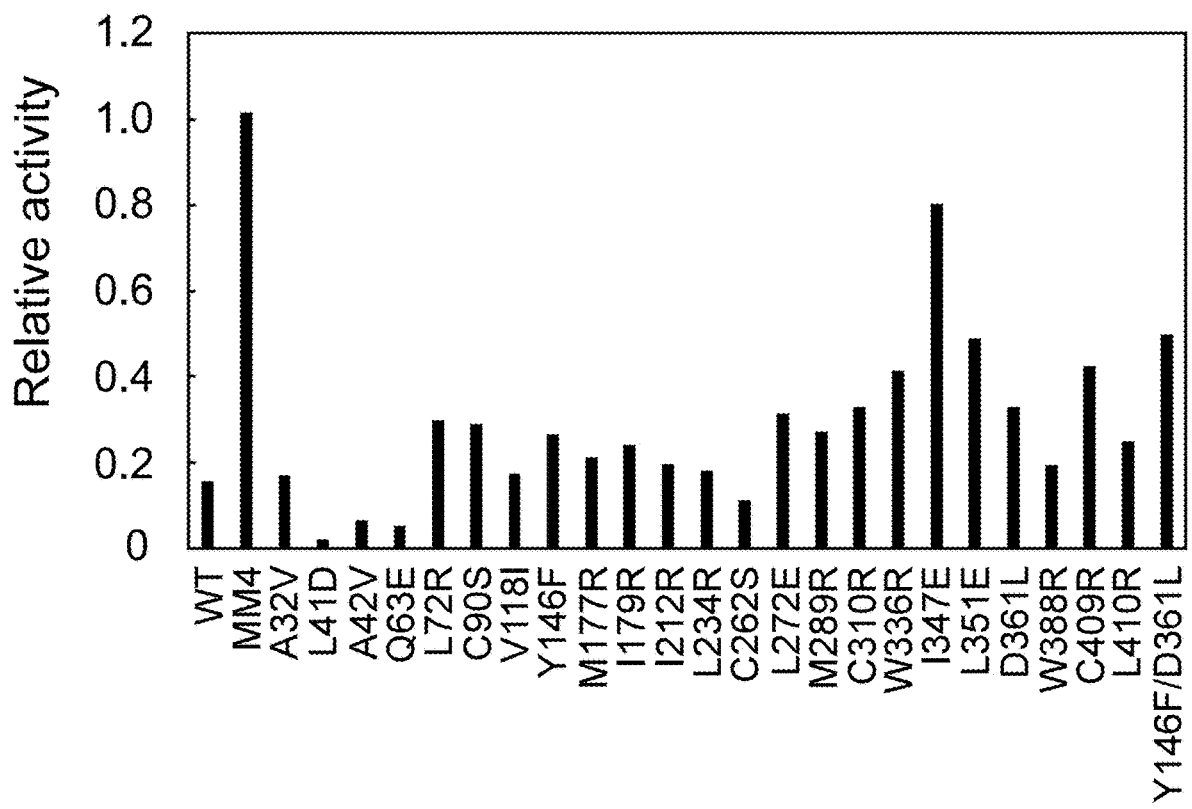

FIGS. 3A-3C: Activity and stability of single variants. (FIG. 3A) Specific activity. The dTTP incorporation reaction was carried out at 37° C. One unit is defined as the amount which incorporates 1 nmol of dTTP into poly(rA)-p(dT)$_{15}$ in 10 min. The relative specific activity is defined as the ratio of the specific activity of variant to that of WT. (FIGS. 3B, 3C) Thermal stability. RT at 100 nM was incubated at 46° C. (FIG. 3B) or 49° C. (FIG. 3C) in the presence of poly(rA)-p(dT)$_{15}$ (28 µM) for 10 min. Then, the dTTP incorporation reaction was carried out at 37° C. The relative activity is defined as the ratio of the initial reaction rate of RT with the 10-min incubation at 46 or 49° C. to that without the incubation.

FIGS. 4A-4F: Activity and stability of multiple variants. (FIGS. 4A, 4B) Specific activity. (FIG. 4A) The dTTP incorporation reaction was carried out at 5 nM RT at 37° C. One unit is defined as the amount which incorporates 1 nmol of dTTP into poly(rA)-p(dT)$_{15}$ in 10 min. The relative specific activity is defined as the ratio of the specific activity of variant to that of WT. (FIG. 4B) The PicoGreen incorporation reaction was carried out at 5 nM RT at 37° C. The initial reaction rates (ΔFI/min) were calculated and normalized with that of WT as 1.0. (FIGS. 4C-4F) Thermal stability. RT at 100 nM was incubated at 49 or 51° C. in the presence of poly(rA)-p(dT)$_{15}$ (28 µM) for 10 min. Then, the dTTP incorporation reaction (FIGS. 4C, 4E) or the PicoGreen incorporation reaction (FIGS. 4D, 4F) was carried out at 10 nM RT at 37° C. The relative activity is defined as the ratio of the initial reaction rate of RT with the 10-min thermal treatment to that without it.

Figure 5A:
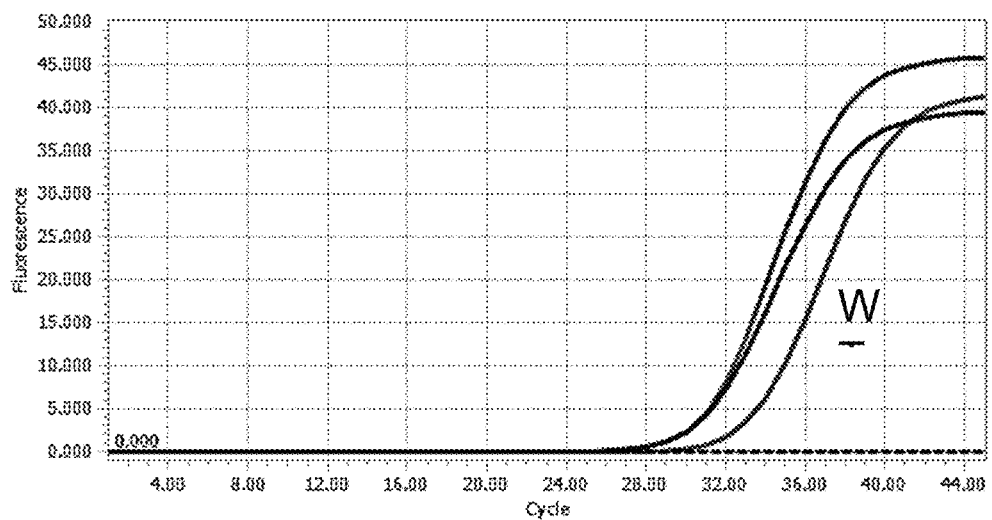
Figure 5B:
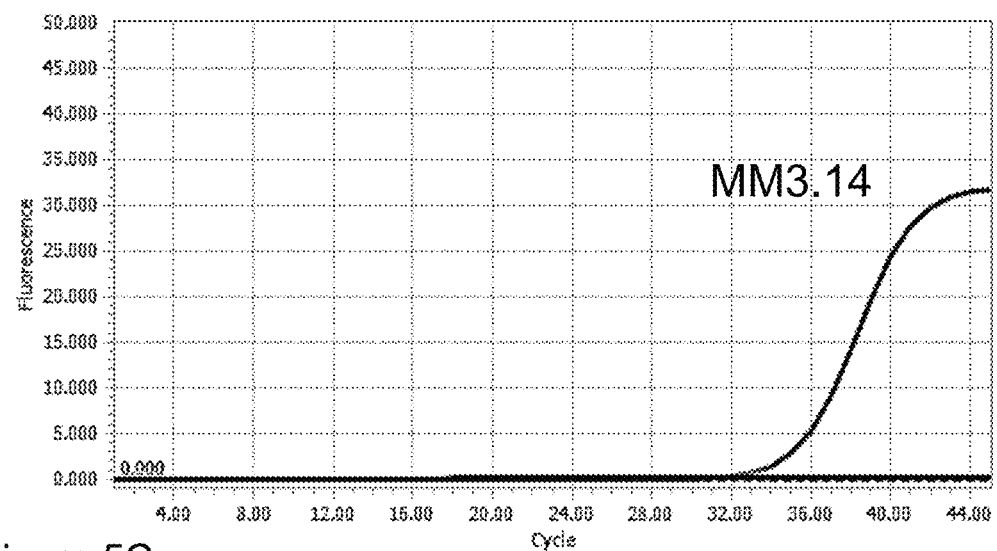
Figure 5C:
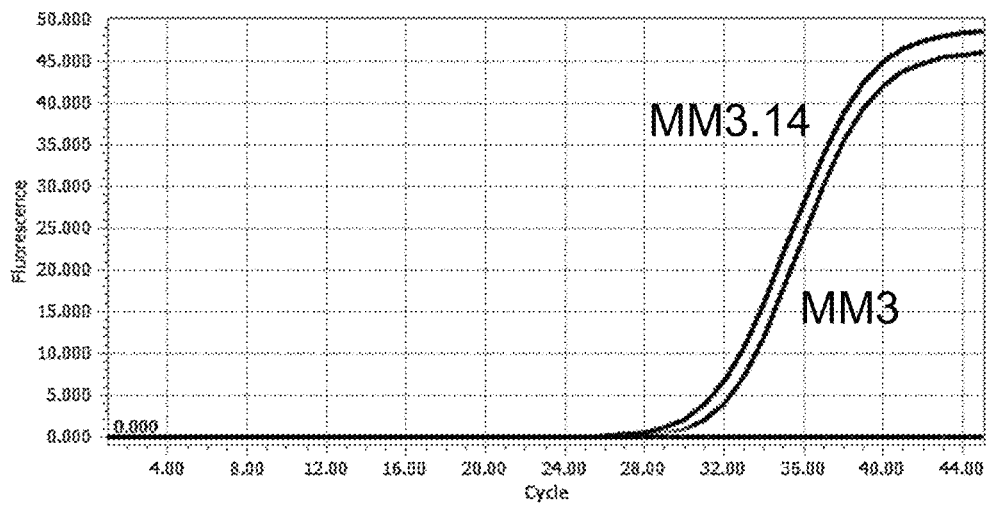
Figure 5D:
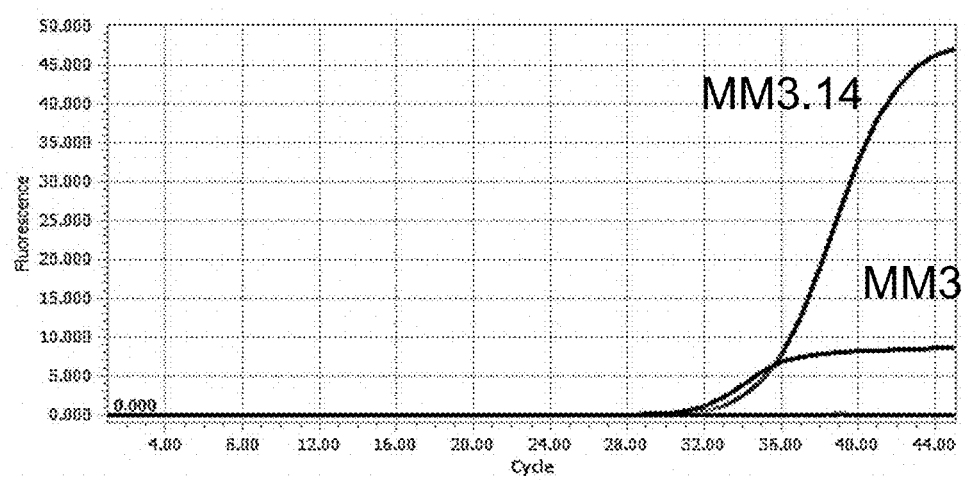
Figure 5E:
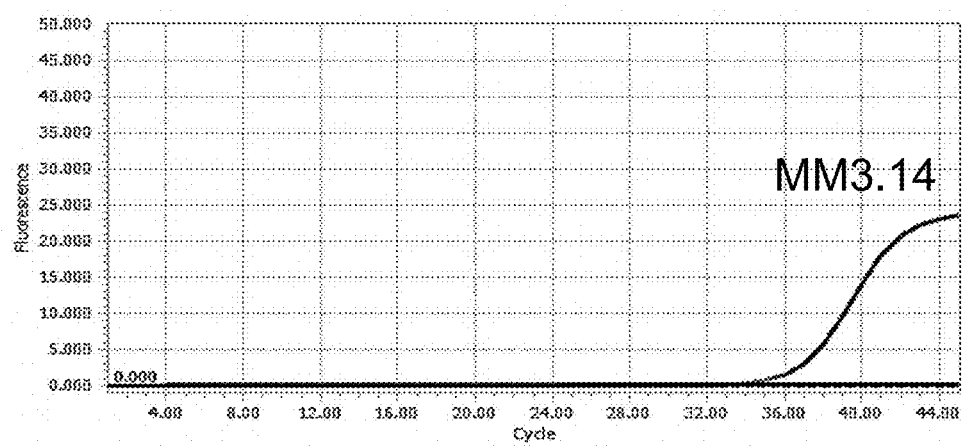

FIGS. 5A-5E: Temperature dependence on cDNA synthesis by WT, MM3, or MM3.14. cDNA synthesis reaction was carried out at 50 (FIG. 5A), 55 (FIGS. 5B, 5C), 60 (FIG. 5D), or 65° C. (FIG. 5E) for 10 min using RT that had received thermal incubation at 55° C. for 5 min (FIG. 5B) or RT without the thermal incubation (FIGS. 5A, 5C-5E). Then, PCR was carried out. Fluorescence of real-time PCR using cDNA synthesis products was shown. The crossing points (CP) were 28.01, 25.22, and 25.67 min for WT, MM3, and MM3.14, respectively (FIG. 5A), 24.95 and 26.74 min for MM3 and MM3.14, respectively (FIG. 5B), 30.52 min for MM3.14 (FIG. 5C), 28.48 and 29.14 min for MM3 and MM3.14, respectively (FIG. 5D), and 32.51 min for MM3.14 (FIG. 5E).

Figure 6:
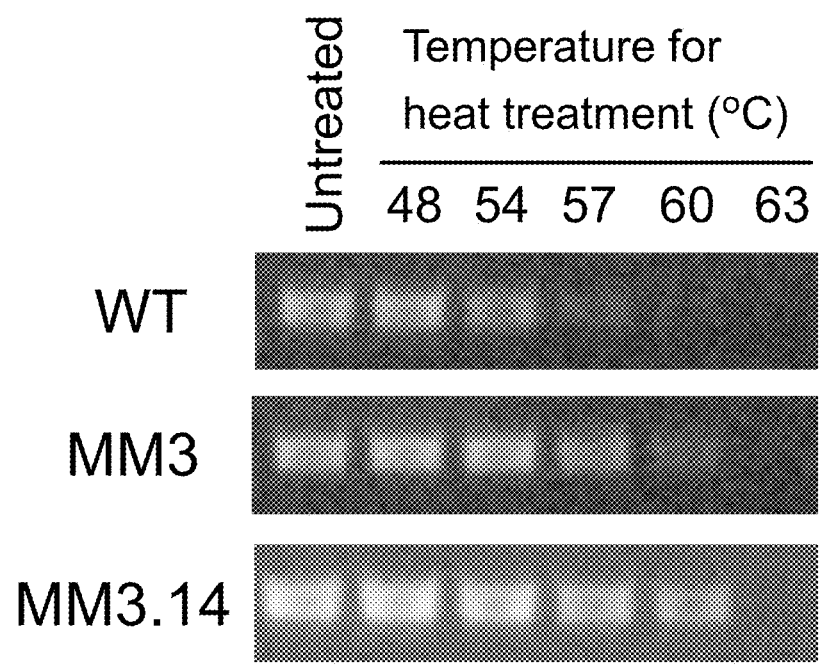

FIG. 6: Stability of WT, MM3, or MM3.14 as assessed by cDNA synthesis. RT at 100 nM was incubated at 48, 54, 57, 60, or 63° C. in the presence of poly(rA)-p(dT)$_{15}$ (28 µM) for 10 min. Then, the cDNA synthesis was carried out with 16 pg cesA RNA, 0.5 µM RV-R26 primer at 45° C. for 30 min. PCR was carried out with a primer combination of RV and F5. Amplified products were applied to 1% agarose gel followed by staining with ethidium bromide (1 µg/ml).

EXAMPLES

Methods

RT Concentration and Standard RNA

RT concentration was determined as according to the method of Bradford (Bradford, 1976) using Protein Assay CBB Solution (Nacalai Tesque, Kyoto, Japan) with bovine serum albumin (Nacalai Tesque) as a standard. Standard RNA, which was an RNA of 1014-nucleotides corresponding to DNA sequence 8353-9366 of the cesA gene of *Bacillus cereus* (GenBank accession number DQ360825), was prepared by in vitro transcription.

Construction of Plasmids

Expression plasmids of MMLV RT variants were constructed by site-directed mutagenesis using the expression plasmid for the wild-type MMLV RT, pET-MRTHis (FIG. 2), or the thermostable variant MM3, pET-MM3, as a template and an *E. coli* BL21(DE3) [F, ompT, hsdSB ($r_B^-$ $m_B^-$) gal dcm (DE3)] as a host. The nucleotide sequences of mutated MMLV RT genes were verified.

Expression and Purification of Single MMLV RT Variants

Three ml of L broth containing 50 µg/ml ampicillin was inoculated with the glycerol stock of the transformed BL21 (DE3) and incubated for 16 h with shaking at 30° C. The expression of the RT gene was induced by the autoinduction system (Novagen, Darmstadt, Germany). MMLV RT was purified from culture medium using HisLink Spin Protein Purification System (Promega, Madison, Wis.). Briefly, the bacterial cells were disrupted by FastBreak Cell Lysis Reagent, followed by addition of HisLink Protein Purification Resin to the culture. The samples were then transferred to HisLink Spin Column where unbound protein was washed away. MMLV RT was recovered by the elution with 0.2 ml of 100 mM HEPES-NaOH buffer (pH 7.5), 500 mM imidazole. The active fraction was desalted using prepacked PD-10 gel filtration columns (GE Healthcare) equilibrated with 50 mM Tris-HCl buffer (pH 8.3), 200 mM KCl, 50% glycerol and stored at −80° C.

Expression and Purification of Multiple MMLV RT Variants

The overnight culture of the transformants (5 mL) was added to 500 mL of L broth containing ampicillin (50 µg/ml) and incubated with shaking at 37° C. When OD$_{660}$ reached 0.6-0.8, 0.15 mL of 0.5 M IPTG was added and growth was continued at 30° C. for 3 h. After centrifugation at 10,000×g for 5 min, the cells were harvested, suspended with 10 mL of 0.02 M potassium phosphate buffer (pH 7.2), 2.0 mM dithiothreitol (DTT), 10% glycerol (buffer A) containing 10 mM phenylmethylsulfonyl fluoride (PMSF), pH 7.5 and disrupted by sonication. After centrifugation at 20,000×g for 40 min, the supernatant was collected and applied to a column [25 mm (inner diameter)×120 mm] packed with Toyopearl DEAE-650M gel (Tosoh, Tokyo, Japan) equilibrated with buffer A. After the washing with buffer A containing 120 mM NaCl, the bound RT was eluted with buffer A containing 300 mM NaCl. Solid (NH$_4$)$_2$SO$_4$ was added to the eluate (30 mL) to a final concentration of 40% saturation. The solution was stirred for 5 min and left for 30 min on ice. After centrifugation at 20,000×g for 30 min at 4° C., the pellet was collected and dissolved in 10 mL of buffer A containing 100 mM NaCl. The solution was applied to the column packed with a Ni$^{2+}$-sepharose (HisTrap HP 1 mL, GE Healthcare, Buckinghamshire, UK) equilibrated with 50 mM Tris-HCl buffer (pH 8.3), 200 mM KCl, 2 mM DTT, 10% glycerol (buffer B). After the washing with buffer B containing 50 mM imidazole, the bound RT was eluted with buffer B containing 500 mM imidazole. The active fraction was desalted using pre-packed PD-10 gel filtration columns equilibrated with 50 mM Tris-HCl buffer (pH 8.3), 200 mM KCl, 50% glycerol and stored at −80° C.

SDS-PAGE

SDS-PAGE was performed in a 10% polyacrylamide gel under reducing conditions. Proteins were reduced by treatment with 2.5% of 2-mercaptoethanol at 100° C. for 10 min, and then applied onto the gel. A constant current of 40 mA was applied for 40 min. After electrophoresis, proteins were stained with Coomassie Brilliant Blue R-250. The molecular mass marker kit consisting of rabbit muscle phosphorylase B (97.2 kDa), bovine serum albumin (66.4 kDa), hen egg white ovalbumin (44.3 kDa), and bovine carbonic anhydrase (29.0 kDa) was a product of Takara Bio Inc (Otsu, Japan).

Reverse Transcription Assay Using [$^3$H]-dTTP poly(rA)-p(dT)$_{15}$ was prepared by annealing (dT)$_{15}$ (Fasmac, Tokyo, Japan) and poly(rA) (GE Healthcare, Buckinghamshire, UK). The reaction was carried out in 25 mM Tris-HCl buffer (pH 8.3), 50 mM KCl, 2 mM DTT, 5 mM MgCl$_2$, 25 µM poly(rA)-p(dT)$_{15}$ (this concentration is expressed based on p(dT)$_{15}$), 0.2 mM [$^3$H]dTTP (1.85 Bq/pmol) (GE Healthcare), and 5 or 10 nM MMLV RT at 37° C. An aliquot (20 µl) was taken from the reaction mixture at 3 and 6 min and immediately spotted onto the glass filter. Unincorporated [³H]dTTP was removed by three washes of chilled 5% (w/v) trichloroacetic acid (TCA) for 10 min each, followed by one wash of chilled 95% ethanol. The radioactivity retained on the dried filters was counted in 2.5 ml of Ecoscint H (National Diagnostics, Yorkshire, UK). The initial reaction rate was estimated from the time-course for incorporation of [³H]dTTP.

Reverse transcription assay using fluorescent dye PicoGreen EnzChek Reverse Transcriptase Assay Kit (Thermo Fisher Scientific, Waltham, Mass.) was used. 20×TE buffer (1 ml) was diluted by adding 19 ml of water to make 1×TE buffer. PicoGreen dsDNA quantification reagent (50 µl) was diluted by adding 17.5 ml of 1×TE buffer to make PicoGreen solution. poly(rA)-p(dT)$_{16}$ for use in thermal inactivation was prepared as follows: poly(rA) (3 µl of 1 mg/ml in 100 mM Tris-HCl buffer (pH 8.1), 0.5 mM EDTA; around 350 base) and p(dT)$_{16}$ (3 µl of 50 µg/ml in 100 mM Tris-HCl buffer (pH 8.1), 0.5 mM EDTA) were mixed and left for 1 h at room temperature followed by the dilution with 114 µl of PDGT (0.01 M potassium phosphate buffer (pH 7.6), 2 mM DTT, 10% glycerol, 0.2% Triton X-100). MMLV RT (8 µl of 500 nM), poly(rA)-p(dT)$_{16}$ (8 µl), and PDGT (64 µl) were mixed to make the MMLV RT concentration 50 nM. The resulting solution (40 µl out of 80 µl) was incubated at 49 or 51° C. for 10 min followed by the incubation on ice for 30 min.

Poly(rA)-p(dT)$_{16}$ for use in reverse transcription assay was prepared as follows: poly(rA) (5 µl) and p(dT)$_{16}$ (5 µl) were mixed and left for 1 h at room temperature followed by the dilution with 2 ml of polymerization buffer (60 mM Tris-HCl burrer (pH 8.1), 60 mM KCl, 8 mM MgCl$_2$, 13 mM DTT, 100 µM dTTP). Poly(rA)-p(dT)$_{16}$ (96 µl) and 40 µl of 25 or 50 nM MMLV RT, either exposed to the thermal treatment or not, were incubated at 37° C. for 10 min. The reaction was initiated by adding the pre-incubated MMLV RT solution (24 µl) to the pre-incubated poly(rA)-p(dT)$_{16}$ solution (96 µl). An aliquot (25 µl) was taken from the reaction mixture at 2.5, 5.0, 7.5, and 10 min, to which 2 µl of 200 mM EDTA was immediately added, followed by the incubation on ice for 30 min or more. Blank solution was prepared by mixing poly(rA)-p(dT)$_{16}$ solution (20 µl) and 200 mM EDTA (2 µl) followed by the addition of MMLV RT solution (5 µl). To each solution (27 µl), PicoGreen solution (173 µl) was added. The tubes were wrapped with aluminum foil and left at room temperature for 10 min. The fluorescence at 523 nm was measured with EnSight (Perkin Elmer) with the excitation wavelength of 502 nm.

cDNA Synthesis

Standard RNA, which is an RNA of 1,014-nucleotides corresponding to DNA sequence 8,353-9,366 of the cesA gene of *Bacillus cereus* (GenBank accession number DQ360825), was prepared by in vitro transcription. The reaction mixture for cDNA synthesis (20 µl) was prepared by mixing water (12 µl), 10×RT buffer (250 mM Tris-HCl buffer (pH 8.3), 500 mM KCl, 20 mM DTT, 50 mM MgCl$_2$) (2 µl), 2.0 mM dNTP (1 µl), 160 µg/µl cesA RNA (2 µl), 10 µM RV-R26 primer 5'-TGTGGAATTGT-GAGCGGTGTCGCAATCACCGTAACACGACGTAG-3' (SEQ ID NO: 4) (1 µl) and 10 nM MMLV RT WT (2 µl). The reaction was run at 45° C. for 30 min and 65° C. for 5 min. The reaction mixture for PCR (25 µl) was prepared by mixing the reaction product of cDNA synthesis (2 µl), water (17.7 µl), 10×PCR buffer (2.5 µl), 2 mM dNTP (1.5 µl), 10 µM F5 primer 5'-TGCGCGCAAAATGGGTATCAC-3' (SEQ ID NO: 5) (0.5 µl) and 10 µM RV primer 5'-TGTG-GAATTGTGAGCGG-3' (SEQ ID NO: 6) (0.5 µl), and Taq polymerase (0.3 µl). The reaction was run under 30 cycles of 30 s at 95° C., 30 s at 55° C., and 60 s at 72° C. The amplified products was separated on 1.0% w/v agarose gels and stained with ethidium bromide (1 µg/ml).

Example 1: Design of Mutations and Characterization of Single Variants

We previously generated a thermostable triple MMLV RT variant MM3 (E286R/E302K/L435R) by introducing positive charges at positions that have been implicated in the interaction with a template-primer (Yasukawa et al., 2010). In order to further stabilize MMLV RT, we designed 29 mutations (Table 1). They are 8 mutations aimed to stabilize hydrophobic core, 8 mutations aimed to introduce salt bridge, 10 mutations aimed to introduce surface charge, and three mutations aimed to avoid disulfide bond.

TABLE 1

Designed mutations

| Mutation | Aim |
| --- | --- |
| Ala32→Val | Stabilize hydrophobic core |
| Leu41→Asp | Introduce salt bridge |
| Ala42→Val | Stabilize hydrophobic core |
| Val43→Glu | Increase surface charge |
| Gln63→Glu | Introduce salt bridge |
| Leu72→Arg | Increase surface charge |
| Cys90→Ser | Avoid disulfide bonds |
| Val118→Ile | Stabilize hydrophobic core |
| Tyr146→Phe | Stabilize hydrophobic core |
| Ala154→Ile | Stabilize hydrophobic core |
| Met177→Arg | Increase surface charge |
| Ile179→Arg | Increase surface charge |
| Ile212→Arg | Increase surface charge |
| Leu234→Arg | Increase surface charge |
| Ile261→Phe | Stabilize hydrophobic core |
| Cys262→Ser | Avoid disulfide bonds |
| Leu272→Glu | Introduce salt bridge |
| Met289→Arg | Increase surface charge |
| Cys310→Leu | Stabilize hydrophobic core |
| Trp336→Arg | Introduce salt bridge |
| Ile347→Glu | Introduce salt bridge |
| Leu351→Glu | Increase surface charge |
| Leu357→Asp | Introduce salt bridge |
| Asp361→Leu | Stabilize hydrophobic core |
| Leu368→Arg | Increase surface charge |
| Val370→Glu | Introduce salt bridge |
| Trp388→Arg | Introduce salt bridge |
| Cys409→Arg | Avoid disulfide bonds |
| Leu410→Arg | Increase surface charge |

The wild-type MMLV RT (WT), the 29 single variants, and one double variant Y146F/D361L were expressed in 3-ml culture and purified from the cells. A thermostable quadruple variant MM4 (E286R/E302K/L435R/D524A) (Yasukawa et al., 2010) was also prepared. MM4 lacks the RNase H activity because Asp524 is a catalytic residue for the RNase H activity. Following SDS-PAGE under reducing conditions, purified WT and variants yielded a single band with a molecular mass of 75 kDa.

FIG. 3A shows the specific activities of the reverse transcription reaction for WT and the 30 variants. The specific activity of WT was 14,000 units/mg. All variants can be classified into three groups. Group 1 comprises V43E, A154I, I261F, L357D, L368R, and V370E whose specific activities were less than 10% of that of WT. Group 2 comprises L41 D, Q63E, L72R, L272E W388R, and L410R whose specific activities were 60-140% of that of WT. Group 3 comprises the other 18 variants whose specific activities were 10-60% of that of WT.

FIGS. 3B and C show the stabilities of WT, MM4, and the 24 variants which belong to Group 2 or 3 at 49 and 51° C., respectively. Relative activity was defined as the ratio of the initial reaction rate for a 10-min incubation at 49 or 51° C. in the presence of T/P to the rate without incubation. The relative activities of WT and D524A at 49° C. were 66 and 120%, respectively, and those at 51° C. were 18 and 100%, respectively. No variants exhibited higher relative activity than MM4 at 49 or 51° C. However, A32V, L72R, L212R, L272E, W388R, and C409R exhibited higher relative activity than WT both at 49 and 51° C.

Example 2: Design of Mutational Combination and Characterization of Multiple Variants Based on the results presented in FIG. 3, four mutations (Ala32→Val, Leu72→Arg, Ile212→Arg, Leu272→Glu, and Trp388→Arg) were selected as the stabilizing mutations and one mutation (Leu41→Asp) was selected as the activating mutation. Ten variants (MM3.1-MM3.10) were designed by combing one, two, or three out of the six mutations with the MM3 mutations (Glu286→Arg, Glu302→Lys, and Leu435→Arg) (Table 2).

TABLE 2

Multiple variants

| Variant | Mutations |
| --- | --- |
| MM3 | E286R/E302K/L435R |
| MM3.1 | E286R/E302K/W388R/L435R |
| MM3.2 | L272E/E286R/E302K/L435R |
| MM3.3 | A32V/E286R/E302K/L435R |
| MM3.4 | L72R/E286R/E302K/L435R |
| MM3.5 | I212R/E286R/E302K/L435R |
| MM3.6 | L41D/E286R/E302K/L435R |
| MM3.7 | I212R/E286R/E302K/W388R/L435R |
| MM3.8 | L72R/E286R/E302K/W388R/L435R |
| MM3.9 | L72R/I212R/E286K/E302K/L435R |
| MM3.10 | L72R/I212R/E286R/E302K/W388R/L435R |
| MM3.11 | A32V/L72R/E286R/E302K/L435R |
| MM3.12 | A32V/I212R/E286R/E302K/L435R |
| MM3.13 | A32V/I212R/E286R/E302K/W388R/L435R |
| MM3.14 | A32V/L72R/E286R/E302K/W388R/L435R |
| MM3.15 | A32V/L72R/I212R/E286R/E302K/W388R/L435R |

They were expressed in *E. coli* and purified. Upon SDS-PAGE under reducing conditions, purified variants yielded a single band with a molecular mass of 75 kDa. The yields of the purified enzymes from 500 ml of culture were in the range of 0.38-4.26 mg, which were comparable to that of the WT (2.27 mg) (Table 3).

TABLE 3

Yield, activity and stability of MMLV RT variants by the assay using using [³H]-dTTP

| Variant | Yields from 500-ml culture (mg) | Specific activity[a] (units/mg) |
| --- | --- | --- |
| WT | 2.27 | 139,000 (1.0)[b] |
| MM3 | 4.26 | 92,000 (0.66)[b] |
| MM3.1 | 0.38 | 39,000 (0.28)[b] |
| MM3.2 | 3.24 | 0 (0)[b] |
| MM3.3 | 2.97 | 53,000 (0.38)[b] |
| MM3.4 | 2.30 | 80,000 (0.58)[b] |
| MM3.5 | 2.45 | 112,000 (0.81)[b] |
| MM3.6 | 2.22 | 103,000 (0.74)[b] |
| MM3.7 | 1.64 | 147,000 (1.1)[b] |
| MM3.8 | 2.65 | 84,000 (0.60)[b] |
| MM3.9 | 2.99 | 80,000 (0.58)[b] |
| MM3.10 | 2.23 | 60,000 (0.43)[b] |

[a]The reaction was carried out in 5 nM RT, 25 mM Tris-HCl buffer (pH 8.3), 50 mM KCl, 2 mM DTT, 5 mM MgCl$_2$, 25 μM poly(rA)-p(dT)$_{15}$ (this concentration is expressed based on p(dT)$_{15}$), and 0.2 mM [³H]dTTP at 37° C. One unit is defined as the amount which incorporates 1 nmol of dTTP into poly(rA)-p(dT)$_{15}$ in 10 min.
[b]Numbers in parentheses indicate values relative to WT (wildtype).

Figure 4A:
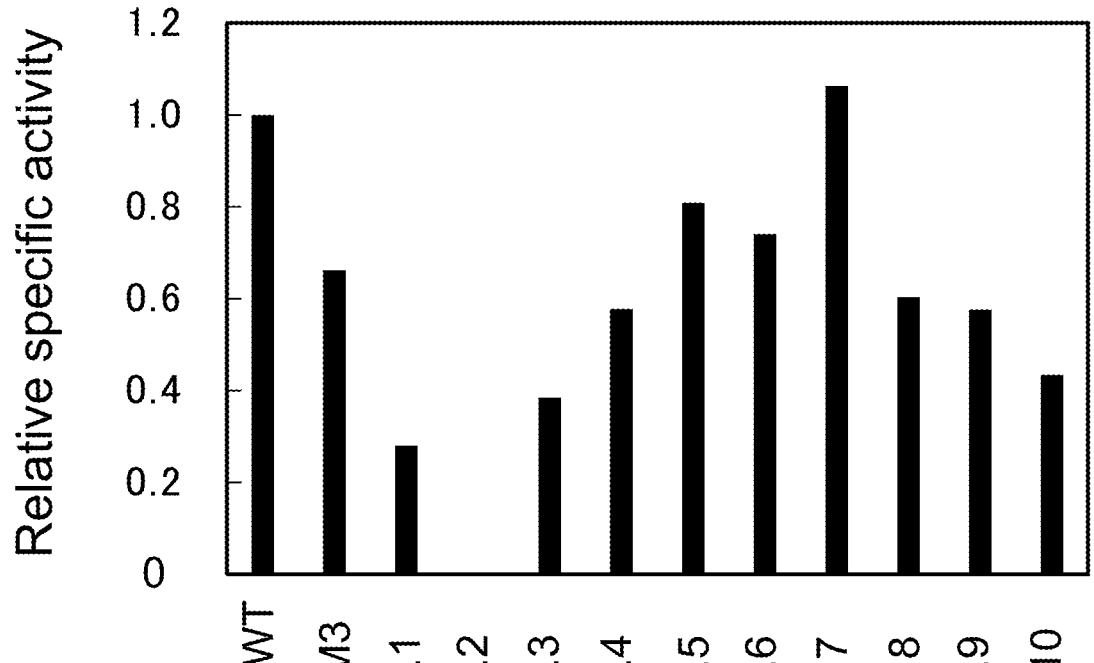
Figure 4B:
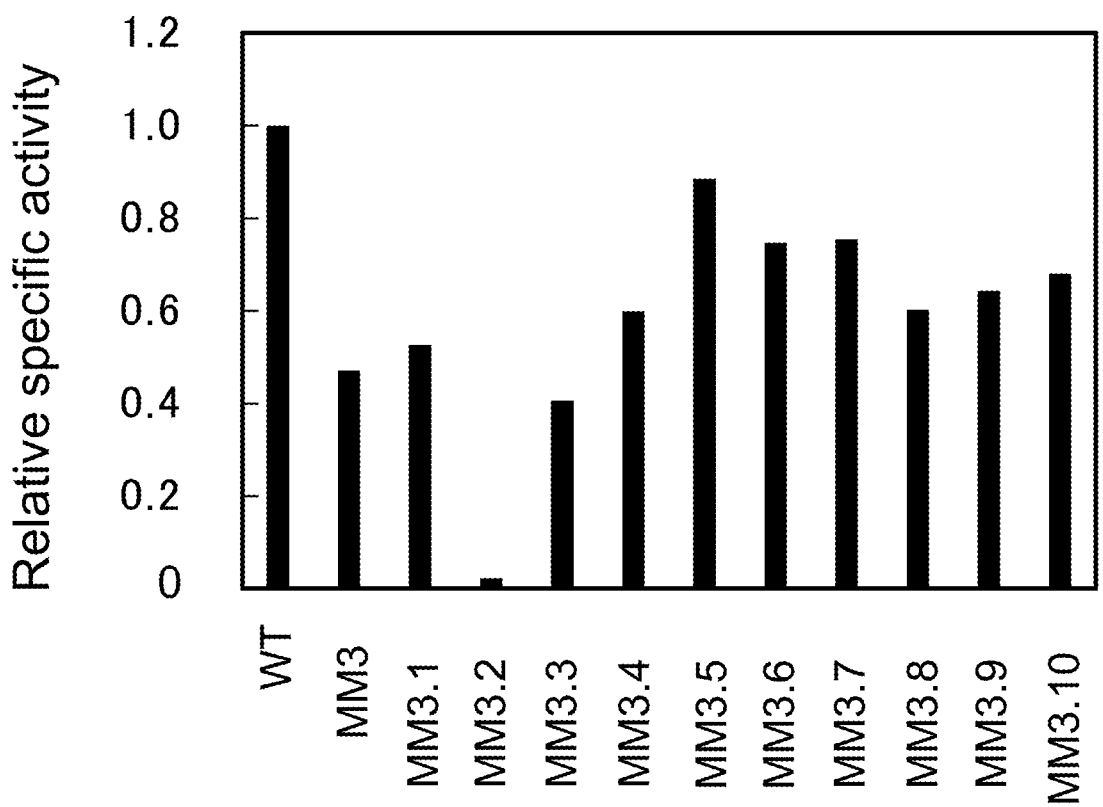
Figure 4C:
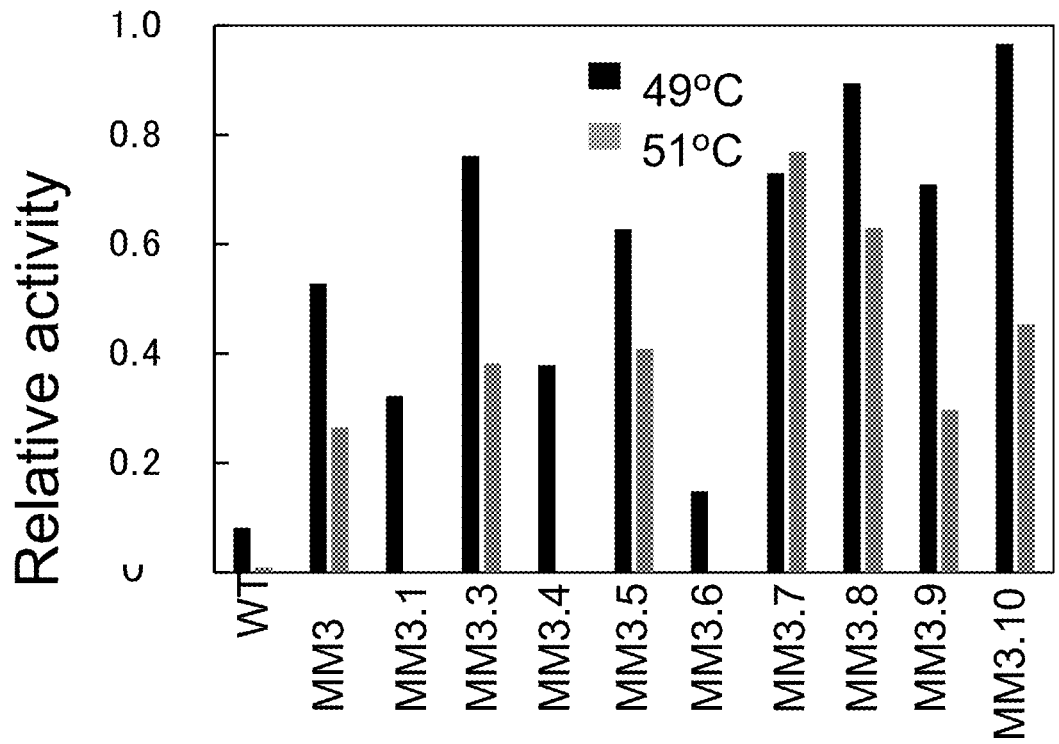

FIG. 4A and Table 3 show the activities by the reverse transcription assay using [³H]-dTTP. Stabilities were assessed by the assay using fluorescent dye PicoGreen. MM3.2 (L272E/E286R/E302K/L435R) lacked the activity, indicating that the mutation of Leu272→Glu was incompatible with the MM3 mutations. The specific activities of the other nine variants (MM3.1 and MM3.3-MM3.10) were 30-100% of that of WT.

TABLE 4

Stability of MMLV RT variants by the assay using [³H]-dTTP.

| | Initial reaction rate (nM/s) | | | |
| --- | --- | --- | --- | --- |
| | Before heat treatment[a] | After heat treatment (49° C.)[b] | Before heat treatment | After heat treatment (51° C.)[b] |
| WT | 70.8 | 5.8 (0.08)[c] | 70.5 | 0.7 (0.0)[c] |
| MM3 | 92.4 | 48.8 (0.53)[c] | 78.8 | 20.9 (0.27)[c] |
| MM3.1 | 33.1 | 10.7 (0.32)[c] | NT[d] | NT[d] |
| MM3.2 | NT[d] | NT[d] | NT[d] | NT[d] |
| MM3.3 | 47.8 | 36.4 (0.76)[c] | 46.2 | 17.6 (0.38)[c] |
| MM3.4 | 96.3 | 36.5 (0.38)[c] | NT[d] | NT[d] |
| MM3.5 | 64.9 | 40.7 (0.63)[c] | 120.7 | 49.4 (0.41)[c] |
| MM3.6 | 60.0 | 8.9 (0.15)[c] | NT[d] | NT[d] |
| MM3.7 | 87.3 | 63.7 (0.73)[c] | 71.9 | 55.3 (0.77)[c] |
| MM3.8 | 73.7 | 65.9 (0.89)[c] | 60.8 | 38.3 (0.63)[c] |
| MM3.9 | 83.0 | 58.9 (0.71)[c] | 47.1 | 14.0 (0.30)[c] |
| MM3.10 | 70.3 | 67.9 (0.97)[c] | 41.2 | 18.7 (0.45)[c] |

Figure 4D:
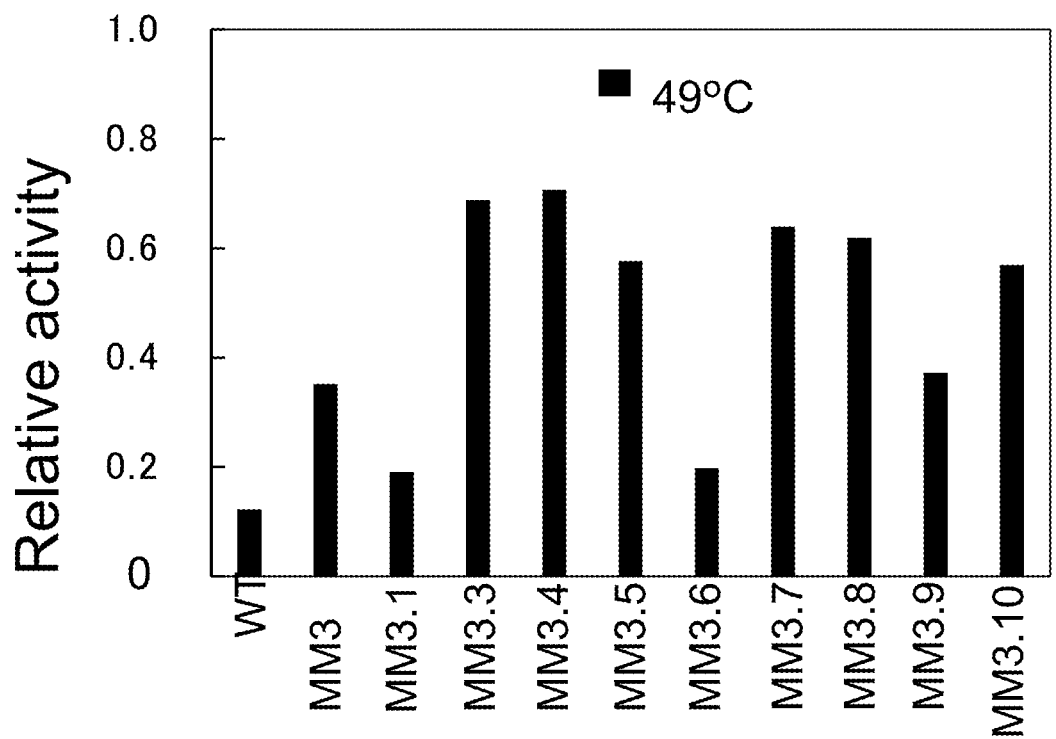

[a]The reaction was carried out in 10 nM RT, 25 mM Tris-HCl buffer (pH 8.3), 50 mM KCl, 2 mM DTT, 5 mM MgCl$_2$, 25 μM poly(rA)-p(dT)$_{15}$ (this concentration is expressed based on p(dT)$_{15}$), and 0.2 mM [³H]dTTP at 37° C. One unit is defined as the amount which incorporates 1 nmol of dTTP into poly(rA)-p(dT)$_{15}$ in 10 min.
[b]RT at 100 nM was incubated at 49 or 51° C. in the absence or presence of poly(rA)-p(dT)$_{15}$ (28 μM) for 10 min. Then, the dTTP incorporation reaction was carried out at 37° C.
[c]Numbers in parentheses indicate the relative activity, which is defined as the ratio of the initial reaction rate with incubation to that without incubation.
[d]Not tested FIG. 4C and Table 4 show the stabilities as assessed by the assay using [³H]-dTTP, and FIG. 4D shows the stabilities as assessed by the assay using PicoGreen. The relative activities of MM3.3 MM3.5, MM3.7, MM3.8, MM3.9, and MM3.10 were comparable to that of MM3 while those of MM3.1, MM3.4, and MM3.6 were lower than MM3. The relative activity of MM3.6 (L41 D/E286R/E302K/L435R) was almost the same to that of WT, indicating that the mutation of Leu41→Asp was incompatible with the MM3 mutations.

Figure 4E:
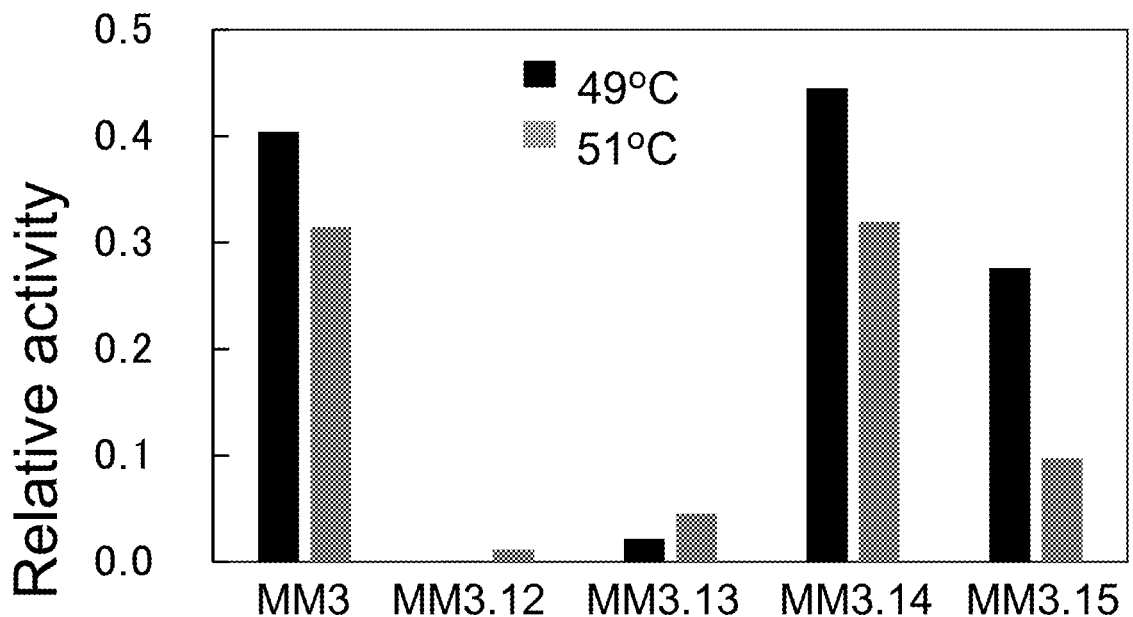
Figure 4F:
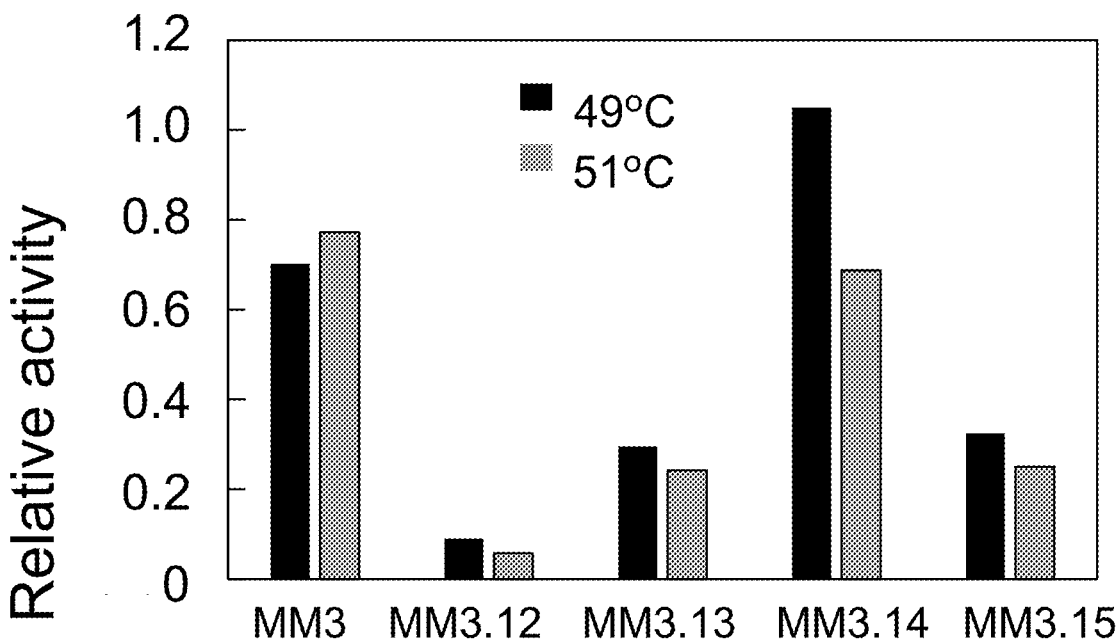

Additionally, five variants (MM3.11-MM3.15; see Table 2) were designed by combing two or more of the four mutations (Ala32→Val, Leu72→Arg, Ile212→Arg, and Trp388→Arg). MM3.11 was not expressed, but the other four variants (MM3.12-MM3.15) were expressed in *E. coli* and purified. FIGS. 4E and 4F show their stabilities as assessed by the assay using [³H]-dTTP and PicoGreen, respectively. The relative activity of MM3.14 was superior to that of MM3 while those of MM3.12, MM3.13, and MM3.15 were lower than MM3.

MM3.14 was further evaluated. FIG. 5 shows the temperature dependence on cDNA synthesis by WT, MM3, or MM3.14. After the cDNA synthesis reaction, real-time PCR was carried out. When cDNA synthesis reaction was conducted with MM3.14 at 55, 60, or 65° C. for 10 min, the fluorescence increased in the PCR. On the other hand, when the cDNA synthesis reaction was conducted with WT or MM3, it was not. This indicates that MM3.14 was more thermostable and more suitable for use in cDNA synthesis than MM3.

FIG. 6 shows the comparison of the thermostabilities of WT, MM3, and MM3.14. The cDNA synthesis reaction was carried out at 45° C. for 30 min with WT, MM3, or MM3.14 exposed to 48-63° C. for 10 min. The reaction product was subjected to PCR, followed by agarose gel electrophoresis. The highest temperatures at which cDNA was synthesized were 60° C. for MM3.

In a further experiment it was proven that cDNA was synthesized at 60 and 65° C. in the reaction with MM3.14 (A32V/L72R/E286R/E302K/W388R/L435R), while it was little synthesized at 60° C. and not synthesized at 65° C. in the reaction with MM3 (E286R/E302K/L435R), indicating that MM3.14 is more thermostable than MM3 in the reaction.

In summary, it could be proven that MM3.14 is more thermostable than MM3.

REFERENCES

Arezi, B. and Hogrefe, H. (2009) Nucleic Acids Res., 37, 473-481.
Baranauskas, A., Paliksa, S., Alzbutas, G., Vaitkevicius, M., Lubiene, J., Letukiene, V., Burinskas, S., Sasnauskas, G. and Skirgaila, R. (2012) Protein Eng. Des. Sel., 25, 657-668.
Bradford, M. M. (1976) Anal Biochem., 72, 248-254
Gerard, G. F., Potter, R. J., Smith, M. D., Rosenthal, K., Dhariwal, G., Lee, J. and
Chatterjee, D. K. (2002) Nucleic Acids Res., 30, 3118-3129
Konishi, A., Ma, X. and Yasukawa, K. (2014) Biosci. Biotechnol. Biochem., 78, 147-150.
Kotewicz, M. L., D'Alessio, J. M., Driftmier, K. M., Blodgett, K. P. and Gerard, G. F. (1985) Gene, 35, 249-258.
Mizuno, M., Yasukawa, K. and Inouye, K. (2010) Biosci. Biotechnol. Biochem., 74, 440-442.
Shoichet, B. K., Baase, W. A., Kuroki, R. and Matthews, B. W. (1995) Proc. Natl. Acad. Sci. U.S.A, 92, 452-456.
Yasukawa, K., Mizuno, M., Konishi, A. and Inouye, K. (2010) J. Biotechnol., 150, 299-306.

The invention claimed is:

1. A method for reverse transcription of a mRNA, the method comprising synthesizing a cDNA from the mRNA using a mutant reverse transcriptase (RT), the mutant RT consisting of
  i) an amino acid sequence that has only six amino acid substitutions of SEQ ID NO: 1, wherein, in SEQ ID NO:1,
    Ala at position 32 is substituted with Val (A32V);
    Leu at position 72 is substituted with Arg (L72R);
    Glu at position 286 is substituted with Arg (E286R);
    Glu at position 302 is substituted with Lys (E302K);
    Trp at position 388 is substituted with Arg (W388R); and
    Leu at position 435 is substituted with Arg (L435R),
    wherein the mutant RT exhibits a reverse transcriptase activity, and wherein the mutant RT also has an increased thermal stability relative to a mutant MM3, wherein the mutant MM3 has an amino acid sequence that differs from the amino acid sequence of SEQ ID NO: 1 and only has three amino acid substitutions of SEQ ID NO: 1, wherein, in SEQ ID NO:1, Glu at position 286 is substituted with Arg (E286R), Glu at position 302 is substituted with Lys (E302K) and Leu at position 435 is substituted with Arg (L435R).

2. The method of claim 1, wherein the reverse transcriptase activity of the mutant RT is at least 50% of the reverse transcriptase activity of the wildtype RT.

3. The method of claim 1, wherein the mutant RT is capable of fusing to another protein.

4. The method of claim 1, wherein the mutant RT consists of SEQ ID NO:2.

* * * * *

SEQUENCE LISTING

```
Sequence total quantity: 11
SEQ ID NO: 1            moltype = AA  length = 671
FEATURE                 Location/Qualifiers
source                  1..671
                        mol_type = protein
                        organism = synthetic construct
SEQUENCE: 1
TLNIEDEHRL HETSKEPDVS LGSTWLSDFP QAWAETGGMG LAVRQAPLII PLKATSTPVS  60
IKQYPMSQEA RLGIKPHIQR LLDQGILVPC QSPWNTPLLP VKKPGTNDYR PVQDLREVNK 120
RVEDIHPTVP NPYNLLSGLP PSHQWYTVLD LKDAFFCLRL HPTSQPLFAF EWRDPEMGIS 180
GQLTWTRLPQ GFKNSPTLFD EALHRDLADF RIQHPDLILL QYVDDLLLAA TSELDCQQGT 240
RALLQTLGNL GYRASAKKAQ ICQKQVKYLG YLLKEGQRWL TEARKETVMG QPTPKTPRQL 300
REFLGTAGFC RLWIPGFAEM AAPLYPLTKT GTLFNWGPDQ QKAYQEIKQA LLTAPALGLP 360
DLTKPFELFV DEKQGYAKGV LTQKLGPWRR PVAYLSKKLD PVAAGWPPCL RMVAAIAVLT 420
KDAGKLTMGQ PLVILAPHAV EALVKQPPDR WLSNARMTHY QALLLDTDRV QFGPVVALNP 480
ATLLPLPEEG LQHNCLDILA EAHGTRPDLT DQPLPDADHT WYTDGSSLLQ EGQRKAGAAV 540
TTETEVIWAK ALPAGTSAQR AELIALTQAL KMAEGKKLNV YTDSRYAFAT AHIHGEIYRR 600
RGLLTSEGKE IKNKDEILAL LKALFLPKRL SIIHCPGHQK GHSAEARGNR MADQAARKAA 660
ITETPDTSTL L                                                     671

SEQ ID NO: 2            moltype = AA  length = 671
FEATURE                 Location/Qualifiers
source                  1..671
                        mol_type = protein
                        organism = synthetic construct
SEQUENCE: 2
TLNIEDEHRL HETSKEPDVS LGSTWLSDFP QVWAETGGMG LAVRQAPLII PLKATSTPVS  60
IKQYPMSQEA RRGIKPHIQR LLDQGILVPC QSPWNTPLLP VKKPGTNDYR PVQDLREVNK 120
RVEDIHPTVP NPYNLLSGLP PSHQWYTVLD LKDAFFCLRL HPTSQPLFAF EWRDPEMGIS 180
GQLTWTRLPQ GFKNSPTLFD EALHRDLADF RIQHPDLILL QYVDDLLLAA TSELDCQQGT 240
RALLQTLGNL GYRASAKKAQ ICQKQVKYLG YLLKEGQRWL TEARKRTVMG QPTPKTPRQL 300
RKFLGTAGFC RLWIPGFAEM AAPLYPLTKT GTLFNWGPDQ QKAYQEIKQA LLTAPALGLP 360
DLTKPFELFV DEKQGYAKGV LTQKLGPRRR PVAYLSKKLD PVAAGWPPCL RMVAAIAVLT 420
KDAGKLTMGQ PLVIRAPHAV EALVKQPPDR WLSNARMTHY QALLLDTDRV QFGPVVALNP 480
ATLLPLPEEG LQHNCLDILA EAHGTRPDLT DQPLPDADHT WYTDGSSLLQ EGQRKAGAAV 540
TTETEVIWAK ALPAGTSAQR AELIALTQAL KMAEGKKLNV YTDSRYAFAT AHIHGEIYRR 600
RGLLTSEGKE IKNKDEILAL LKALFLPKRL SIIHCPGHQK GHSAEARGNR MADQAARKAA 660
ITETPDTSTL L                                                     671

SEQ ID NO: 3            moltype = DNA  length = 2013
FEATURE                 Location/Qualifiers
source                  1..2013
                        mol_type = other DNA
                        organism = synthetic construct
SEQUENCE: 3
```

```
accctaaata tagaagatga gcatcggcta catgagacct caaaagagcc agatgtttct    60
ctagggtcca catggctgtc tgattttcct caggtctggg cggaaaccgg gggcatggga   120
ctggcagttc gccaagctcc tctgatcata cctctgaaag caacctctac ccccgtgtcc   180
ataaaacaat accccatgtc acaagaagcc agacggggga tcaagcccca catacagaga   240
ctgttggacc agggaatact ggtaccctgc cagtcccct ggaacacgcc cctgctaccc    300
gttaagaaac cagggactaa tgattatagg cctgtccagg atctgagaga agtcaacaag   360
cgggtggaag acatccaccc caccgtgccc aaccccttaca acctcttgag cgggctccca   420
ccgtcccacc agtggtacac tgtgcttgat ttaaaggatg cctttttctg cctgagactc   480
caccccacca gtcagcctct cttcgccttt gagtggagag atccagagat gggaatctca   540
ggacaattga cctggaccag actcccacag ggtttcaaaa acagtcccac cctgtttgat   600
gaggcactgc acagagacct agcagacttc cggatccagc acccagactt gatcctgcta   660
cagtacgtga tgactttact gctggccgcc acttctgagc tagactgcca acaaggtact   720
cgggccctgt tacaaaccct agggaacctc gggtatcggg cctcggccaa gaaagcccaa   780
atttgccaga aacaggtcaa gtatctgggg tatcttctaa aagagggtca gagatggctg   840
actgaggcca gaaaacgtac tgtgatgggg cagcctactc cgaagacccc tcgacaacta   900
aggaagttcc tagggacggc aggcttctgt cgcctctgga tccctgggtt tgcagaaatg   960
gcagcccct  tgtaccctct caccaaaacg gggactctgt ttaattgggg cccagaccaa  1020
caaaaggcct atcaagaaat caagcaagct cttctaactg ccccagccct ggggttgcca  1080
gatttgacta agccctttga actctttgtc gacgagaagc agggctacgc caaaggtgtc  1140
ctaacgcaaa aactgggacc tcggcgtcgg ccggtggcct acctgtccaa aaagctagac  1200
ccagtagcag ctggggtggcc cccttgccta cggatggtag cagccattgc cgtactgaca  1260
aaggatgcag gcaagctaac catgggacag ccactagtca ttcgcgcccc ccatgcagta  1320
gaggcactag tcaaacaacc ccccgaccgc tggcttttcca acgcccggat gactcactat  1380
caggccttgc ttttggacac ggaccgggtc cagttcggac cggtggtagc cctgaacccg  1440
gctacgctgc tcccactgcc tgaggaaggg ctgcaacaca actgcttga tatcctggcc    1500
gaagcccacg gaacccgacc cgacctaacg gaccagccgc tcccagacgc taccacacg   1560
tggtacacgg atggaagcag tctcttacaa gagggacagc gtaaggcggg agctgcggtg  1620
accaccgaga ccgaggtaat ctgggctaaa gccctgccag ccgggacatc cgctcagcgg  1680
gctgaactga tagcactcac ccaggcccta aagatgcag aaggtaagaa gctaaatgtt    1740
tatactgata gccgttatgc ttttgctact gcccatatcc atggagaaat atacagaagg  1800
cgtgggttgc tcacatcaga aggcaaagag atcaaaaata agacgagat cttggcccta    1860
ctaaaagccc tctttctgcc caaaagactt agcataatcc attgtccagg acatcaaaag  1920
ggacacagcg ccgaggctag aggcaaccgg atggctgacc aagcggcccg aaaggcagcc  1980
atcacagaga ctcagacac ctctaccctc ctc                                2013
```
```
SEQ ID NO: 4          moltype = DNA   length = 44
FEATURE               Location/Qualifiers
source                1..44
                      mol_type = other DNA
                      organism = synthetic construct
SEQUENCE: 4
tgtggaattg tgagcggtgt cgcaatcacc gtaacacgac gtag                     44

SEQ ID NO: 5          moltype = DNA   length = 21
FEATURE               Location/Qualifiers
source                1..21
                      mol_type = other DNA
                      organism = synthetic construct
SEQUENCE: 5
tgcgcgcaaa atgggtatca c                                              21

SEQ ID NO: 6          moltype = DNA   length = 17
FEATURE               Location/Qualifiers
source                1..17
                      mol_type = other DNA
                      organism = synthetic construct
SEQUENCE: 6
tgtggaattg tgagcgg                                                   17

SEQ ID NO: 7          moltype = DNA   length = 2013
FEATURE               Location/Qualifiers
source                1..2013
                      mol_type = other DNA
                      organism = synthetic construct
SEQUENCE: 7
accctaaata tagaagatga gcatcggcta catgagacct caaaagagcc agatgtttct    60
ctagggtcca catggctgtc tgattttcct caggcctggg cggaaaccgg gggcatggga   120
ctggcagttc gccaagctcc tctgatcata cctctgaaag caacctctac ccccgtgtcc   180
ataaaacaat accccatgtc acaagaagcc agactgggga tcaagcccca catacagaga   240
ctgttggacc agggaatact ggtaccctgc cagtcccct ggaacacgcc cctgctaccc    300
gttaagaaac cagggactaa tgattatagg cctgtccagg atctgagaga agtcaacaag   360
cgggtggaag acatccaccc caccgtgccc aaccccttaca acctcttgag cgggctccca   420
ccgtcccacc agtggtacac tgtgcttgat ttaaaggatg cctttttctg cctgagactc   480
caccccacca gtcagcctct cttcgccttt gagtggagag atccagagat gggaatctca   540
ggacaattga cctggaccag actcccacag ggtttcaaaa acagtcccac cctgtttgat   600
gaggcactgc acagagacct agcagacttc cggatccagc acccagactt gatcctgcta   660
cagtacgtga tgactttact gctggccgcc acttctgagc tagactgcca acaaggtact   720
cgggccctgt tacaaaccct agggaacctc gggtatcggg cctcggccaa gaaagcccaa   780
atttgccaga aacaggtcaa gtatctgggg tatcttctaa aagagggtca gagatggctg   840
```

```
actgaggcca gaaaagagac tgtgatgggg cagcctactc cgaagacccc tcgacaacta    900
agggagttcc tagggacggc aggcttctgt cgcctctgga tccctgggtt tgcagaaatg    960
gcagcccct  tgtaccctct caccaaaacg gggactctgt ttaattgggg cccagaccaa   1020
caaaaggcct atcaagaaat caagcaagct cttctaactg ccccagccct ggggttgcca   1080
gatttgacta agcccttga  actctttgtc gacgagaagc agggctacgc caaaggtgtc   1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtca ttctggcccc ccatgcagta   1320
gaggcactag tcaaacaacc ccccgaccgc tggctttcca cagcccggat gactcactat   1380
caggccttgc ttttggacac ggacgggtc  cagttcggac cggtggtagc cctgaacccg   1440
gctacgctgc tcccactgcc tgaggaaggg ctgcaacaca actgccttga tatcctggcc   1500
gaagcccacg gaacccgacc cgacctaacg gaccagccgc tcccagacgc cgaccacacc   1560
tggtacacgg atggaagcag tctcttacaa gagggacagc gtaaggcggg agctgcggtg   1620
accaccgaga ccgaggtaat ctgggctaaa gccctgccag ccgggacatc cgctcagcgg   1680
gctgaactga tagcactcac ccaggcccta aagatggcag aaggtaagaa gctaaatgtt   1740
tatactgata gccgttatgc ttttgctact gcccatatcc atggagaaat atacagaagg   1800
cgtgggttgc tcacatcaga aggcaaagag atcaaaaata aagacgagat cttggcccta   1860
ctaaaagccc tcttctctgcc caaaagactt agcataatcc attgtccagg acatcaaaag   1920
ggacacagcg ccgaggctag aggcaaccgg atggctgacc aagcggcccg aaaggcagcc   1980
atcacagaga ctccagacac ctctaccctc ctc                                2013

SEQ ID NO: 8              moltype = DNA  length = 27
FEATURE                   Location/Qualifiers
source                    1..27
                          mol_type = other DNA
                          organism = synthetic construct
SEQUENCE: 8
atgacatggc tgtctgattt tcctcag                                         27

SEQ ID NO: 9              moltype = AA  length = 9
FEATURE                   Location/Qualifiers
source                    1..9
                          mol_type = protein
                          organism = synthetic construct
SEQUENCE: 9
MTWLSDFPQ                                                              9

SEQ ID NO: 10             moltype = DNA  length = 42
FEATURE                   Location/Qualifiers
source                    1..42
                          mol_type = other DNA
                          organism = synthetic construct
SEQUENCE: 10
ccagacacct taccctcct ccaccaccac catcaccact ag                          42

SEQ ID NO: 11             moltype = AA  length = 13
FEATURE                   Location/Qualifiers
source                    1..13
                          mol_type = protein
                          organism = synthetic construct
SEQUENCE: 11
PDTSTLLHHH HHH                                                         13
```